US012805850B2

(12) United States Patent
Franck et al.

(10) Patent No.: US 12,805,850 B2
(45) Date of Patent: Nov. 24, 2026

(54) DEVICES, METHODS AND SYSTEMS FOR SAMPLING AND ANALYZING THE GASTROINTESTINAL TRACT

(71) Applicant: EnteroTrack, LLC, Lafayette, CO (US)

(72) Inventors: Ethan Franck, Denver, CO (US); Jeffrey Brown, Centennial, CO (US)

(73) Assignee: EnteroTrack, LLC, Aurora, CO (US)

( * ) Notice: Subject to any disclaimer, the term of this patent is extended or adjusted under 35 U.S.C. 154(b) by 563 days.

(21) Appl. No.: 18/217,801

(22) Filed: Jul. 3, 2023

(65) Prior Publication Data

US 2024/0016480 A1 Jan. 18, 2024

Related U.S. Application Data

(63) Continuation of application No. PCT/US2022/011128, filed on Jan. 4, 2022.

(Continued)

(51) Int. Cl.
*A61B 10/00* (2006.01)
*A61B 10/02* (2006.01)
(Continued)

(52) U.S. Cl.
CPC .. *A61B 10/0045* (2013.01); *A61B 2010/0061* (2013.01); *A61B 2010/0216* (2013.01); *A61B 10/04* (2013.01); *A61K 9/4808* (2013.01)

(58) Field of Classification Search
CPC ........ A61B 10/0045; A61B 2010/0061; A61B 2010/0216; A61B 10/04; A61K 9/4808
See application file for complete search history.

(56) References Cited

U.S. PATENT DOCUMENTS 2,508,690 A * 5/1950 Egon .................... A61M 25/01 206/438
2,773,502 A * 12/1956 Kaslow ................ A61M 31/00 604/93.01
(Continued)

FOREIGN PATENT DOCUMENTS

CA 2224551 A1 * 8/1999 ....... G01N 33/54388
CN 111214259 B * 8/2024 ......... A61B 10/0045
(Continued)

OTHER PUBLICATIONS

Straumann et al., "Idiopathic eosinophilic esophagitis is associated with a T(H)2-type allergic inflammatory response," J. Allergy Clin. Immunol., 108:954-61, 2001.
(Continued)

*Primary Examiner* — Sean P Dougherty
(74) *Attorney, Agent, or Firm* — Polsinelli PC

(57) ABSTRACT

Embodiments of the instant application are directed to improved devices for sampling the gastrointestinal tract of a subject. In some embodiments, the device includes at least an ingestible capsule having 2 parts for housing an adjustable line or drag material having at least a proximal and distal segment. In some embodiments, the distal segment includes a multi-ply material capable of absorbing fluids and/or further including capture agents. In certain embodiments, the improved devices of the instant application include assessing a condition of the upper gastrointestinal tract of a subject including, but not limited to the esophagus and stomach of the subject.

27 Claims, 5 Drawing Sheets

Related U.S. Application Data

(60) Provisional application No. 63/133,712, filed on Jan. 4, 2021.

(51) Int. Cl.
*A61B 10/04* (2006.01)
*A61K 9/48* (2006.01)

(56) References Cited

U.S. PATENT DOCUMENTS

| | | | | |
|---|---|---|---|---|
| 3,155,091 | A * | 11/1964 | Nissenbaum | A61M 25/0108 600/572 |
| 3,421,499 | A * | 1/1969 | Bray | A61B 5/02042 600/371 |
| 3,528,429 | A * | 9/1970 | Beal | A61B 10/02 600/572 |
| 3,683,890 | A * | 8/1972 | Beal | A61B 10/02 600/431 |
| 4,735,214 | A | 4/1988 | Berman | |
| 5,738,110 | A | 4/1998 | Beal et al. | |
| 5,947,118 | A | 9/1999 | Hochrainer et al. | |
| 6,475,145 | B1 | 11/2002 | Baylor | |
| 7,037,275 | B1 | 5/2006 | Marshall et al. | |
| 7,295,226 | B1 | 11/2007 | Meron | |
| 8,637,239 | B2 | 1/2014 | Furuta et al. | |
| 8,709,736 | B2 | 4/2014 | Lao-Sirieix et al. | |
| 9,372,186 | B2 | 6/2016 | Furuta et al. | |
| 9,980,634 | B2 | 5/2018 | Furuta et al. | |
| 10,292,687 | B2 | 5/2019 | Maguire et al. | |
| 10,674,901 | B2 | 6/2020 | Furuta et al. | |
| 11,246,536 | B2 | 2/2022 | Mccullough | |
| 2006/0073561 | A1 | 4/2006 | Rosen et al. | |
| 2006/0231110 | A1 | 10/2006 | Mintechv | |
| 2007/0021360 | A1 | 1/2007 | Nyce et al. | |
| 2007/0161851 | A1 | 7/2007 | Takizawa | |
| 2007/0238942 | A1 | 10/2007 | Baylor | |
| 2009/0286237 | A1 | 11/2009 | Fitzgerald | |
| 2009/0292167 | A1 | 11/2009 | Kimoto | |
| 2010/0300922 | A1 | 12/2010 | Gilad | |
| 2011/0031150 | A1 | 2/2011 | Trigg | |
| 2012/0226189 | A1 | 9/2012 | Fitzgerald | |
| 2014/0323908 | A1 | 10/2014 | Fitzgerald et al. | |
| 2015/0168409 | A1 | 6/2015 | Di Pietro et al. | |
| 2016/0003827 | A1 | 1/2016 | Fitzgerald et al. | |
| 2016/0045189 | A1* | 2/2016 | Maguire | A61B 10/02 600/572 |
| 2016/0081672 | A1* | 3/2016 | Lubinski | A61B 10/02 600/572 |
| 2016/0081677 | A1* | 3/2016 | Lubinski | A61B 10/04 600/572 |
| 2018/0208991 | A1 | 7/2018 | Fitzgerald et al. | |
| 2020/0352430 | A1 | 11/2020 | Furuta et al. | |
| 2021/0307731 | A1* | 10/2021 | Grayson | A61B 10/0051 |
| 2021/0393172 | A1 | 12/2021 | Eren | |

FOREIGN PATENT DOCUMENTS

| | | | | |
|---|---|---|---|---|
| EP | 1269918 | A1 * | 1/2003 | A61B 10/0045 |
| GB | 1000078 | A | 8/1965 | |
| JP | H09108227 | A | 4/1997 | |
| JP | 2003508106 | A * | 3/2003 | A61B 10/0045 |
| JP | 2013542016 | A | 11/2013 | |
| WO | 9944066 | A1 | 9/1999 | |
| WO | WO-0115604 | A1 * | 3/2001 | A61B 10/02 |
| WO | WO2009/061819 | A1 | 5/2009 | |
| WO | WO2020/104787 | A1 | 5/2020 | |
| WO | WO-2021212031 | A1 * | 10/2021 | C12Q 1/686 |
| WO | WO-2022109425 | A1 * | 5/2022 | A61B 10/0045 |
| WO | WO-2022147536 | A1 * | 7/2022 | A61K 9/4808 |

OTHER PUBLICATIONS

Thibeault et al., "Gene expression changes of inflammatory mediators in posterior laryngitis due to laryngopharyngeal reflux and evolution with PPI treatment: a preliminary study," Laryngoscope, 117:2050-6, 2007.

Thomas et al., "Use of the enterotest duodenal capsule in the diagnosis of giardiasis. A preliminary study," S. Afr. Med. J., 48:2219-20, 1974.

Walsh et al., "Allergic esophagitis in children: a clinicopathological entity," Am. J. Surg. Pathol., 23:390-6, 1999.

Yoshida et al., "Interleukin-8 expression in the esophageal mucosa of patients with gastroesophageal reflux disease," Scand J. Gastroenterol., 39:816-22, 2004.

Yu et al., "Intestinal epithelial CD23 mediates enhanced antigen transport in allergy: evidence for novel splice forms," Am. J. Physiol. Gastrointest. Liver Physiol., 285:G223-34, 2003.

Roth et al., "A comparison of a string test-PCR assay and a stool antigen immunoassay (HpSA) for Helicobacter," (2001) 95, 398-399 pylori screening in Peru (Year: 2001)—U.S. Appl. No. 16/871,987.

Ackerman et al., "Chapter 2: Human eosinophil lysophospholipase (charcot-leyden crystal proten): molecular cloning, expression, and potential functions in asthma," In: Eosinophils in Allergy and Inflammation, Gleich and Kay (Eds.) Marcel Dekker, NY, pp. 21-54, 1994.

Ackerman et al., "Charcot-Leyden crystal protein (galectin-10) is not a dual function galectin with lysophospholipase activity but binds a lysophospholipase inhibitor in a novel structural fashion," J. Biol. Chem., 277:4859-68, 2002.

Ackerman et al., "The human eosinophil Charcot-Leyden crystal protein: biochemical characteristics and measurement by radioimmunoassay," J. Immunol., 125:2118-26, 1980.

Ackerman et al., "Eosinophilia and elevated serum levels of eosinophil major basic protein and Charcot-Leyden crystal protein (lysophospholipase) after treatment of patients with Bancroft's filariasis," J. Immunol., 127:1093-8, 1981.

Ackerman et al., "Eosinophil degranulation. An immunologic determinant in the pathogenesis of the Mazzotti reaction in human onchocerciasis," J. Immunol., 144:3961-9, 1990.

Ackerman et al., "Molecular cloning and characterization of human eosinophil Charcot-Leyden crystal protein (lysophospholipase). Similarities to IgE binding proteins and the S-type animal lectin superfamily," I Immunol., 150:456-68, 1993.

Straumann et al., "Eosinophilic esophagitis: red on microscopy, white on endoscopy," Digestion, 70:109-16, 2004.

Arora and Yamazaki, "Eosinophilic esophagitis: asthma of the esophagus?" Clin. Gastrointest. Nutr., 2:523-30, 2004.

Bevilacqua et al., "Food allergens are protected from degradation during CD23-mediated transepithelial transport," Int. Arch. Allergy Immunol., 135:108-16, 2004.

Blanchard et al., "Eosinophilic esophagitis: pathogenesis, genetics, and therapy," J. Allergy Clin. Immunol., 118:1054-9, 2006.

Blanchard et al., "Eotaxin-3 and a uniquely conserved gene-expression profile in eosinophilic esophagitis," J. Clin. Invest., 116:536-47, 2006.

Foroughi and Prussin, "Clinical management of eosinophilic gastrointestinal disorders," Curr. Allergy Asthma. Rep., 5:259-61, 2005.

Fox et al., "Eosinophilic esophagitis: it's not just kid's stuff," Gastrointest. Endosc., 56:260-70, 2002.

Furuta et al., "Eosinophils alter colonic epithelial barrier function: role for major basic protein," J. Physiol. Gastrointest. Liver Physiol., 289:G890-7, 2005.

Furuta et al., "Eosinophilic esophagitis in children and adults: a systematic review and consensus recommendations for diagnosis and treatment," Gastroenterology, 133: 1342-63, 2007.

Furuta et al., "Hypoxia-inducible factor I-dependent induction of intestinal trefoil factor protects barrier function during hypoxia," J. Exp. Med., 193:1027-34, 2001.

Furuta et al., "Emerging questions regarding eosinophil's role in the esophago-gastrointestinal tract," Opin. Gastroenterol., 22:658-63, 2006.

Furuta et al., "Parallel induction of epithelial surface-associated chemokine and proteoglycan by cellular hypoxia: implications for neutrophil activation," I Leukoc., 68:251-9, 2000.

(56) References Cited

OTHER PUBLICATIONS

Genta et al., "The twentieth eosinophil," Adv. Anat. Pathol., 14:340-3, 2007.
Gomes et al., "Eosinophil-fibroblast interactions induce fibroblast IL-6 secretion and extracellular matrix gene expression: implications in fibrogenesis," J. Allergy Clin. Immunol., 116:796-804, 2005.
Gonsalves et al., "Histopathologic variability and endoscopic correlates in adults with eosinophilic esophagitis," Gastrointest. Endosc., 64:313-9, 2006.
Gowan et al., "Application of meso scale technology for the measurement of phosphoproteins in human tumor xenografts," Assay Drug. Dev. Technol., 5:391-401, 2007.
Gracey et al., "Use of a simple duodenal capsule to study upper intestinal microflora," Arch. Dis. Child, 52:74-6, 1977.
Gupta et al., "Cysteinyl leukotriene levels in esophageal mucosal biopsies of children with eosinophilic inflammation: are they all the same?" Am. I Gastroenterol., 101:1125-8, 2006.
Gupta et al., "Cytokine expression in normal and inflamed esophageal mucosa: a study into the pathogenesis of allergic eosinophilic esophagitis," J. Pediatr. Gastroenterol. Nutr., 42:22-6, 2006.
Gupta et al., "Eosinophilic esophagitis," Ear Nose Throat J., 84:632-3, 2005.
Hogan et al., "Eosinophil Function in Eosinophil-associated Gastrointestinal Disorders," Curr. Allergy Asthma. Rep., 6:65-71, 2006.
Isomoto et al., "Enhanced expression of interleukin-8 and activation of nuclear factor kappa-B in endoscopy-negative gastroesophageal reflux disease," Am. J. Gastroenterol., 99:589-97, 2004.
Kagalwalla et al., "Effect of six-food elimination diet on clinical and histologic outcomes in eosinophilic esophagitis," Clin. Gastroenterol. Hepatol., 4:1097-102, 2006.
Karhausen et al., "Epithelial hypoxia-inducible factor-1 is protective in murine experimental colitis," J. Clin. Invest., 114 1098-106, 2004.
Kirsch et al., "Activated mucosal mast cells differentiate eosinophilic (allergic) esophagitis from gastroesophageal reflux disease," J Pediatr. Gastroenterol. Nutr., 44:20-6, 2007.
Konikoff et al., "Potential of blood eosinophils, eosinophil-derived neurotoxin, and eotaxin-3 as biomarkers of eosinophilic esophagitis," Clin. Gastroenterol. Hepatol., 4:1328-36, 2006.
Li et al., "Transcytosis of IgE-antigen complexes by CD23a in human intestinal epithelial cells and its role in food allergy," Gastroenterology, 131:47-58, 2006.
Liacouras et al., "Eosinophilic esophagitis: a 10-year experience in 381 children," Clin. Gastroenterol. Hepatol., 3:1198-206, 2005.
Mekjavic and Rempel, "Determination of esophageal probe insertion length based on standing and sitting height," J. Appl. Physiol., 69:376-9, 1990.
Mishra et al., "An etiological role for aeroallergens and eosinophils in experimental esophagitis," J. Clin. Invest., 107:83-90, 2001.
Mishra et al., "Critical role for adaptive T cell immunity in experimental eosinophilic esophagitis in mice," J. Leukoc. Biol., 81:916-24, 2007.
Mishra et al., "IL-5 promotes eosinophil trafficking to the esophagus," J. Immunol., 168:2464-9, 2002.
Mishra et al., "Peyer's patch eosinophils: identification, characterization, and regulation by mucosal allergen exposure, interleukin-5, and eotaxin," Blood, 96:1538-44, 2000.
Montagnac et al., "Differential role for CD23 splice forms in apical to basolateral transcytosis of IgE/allergen complexes," Traffic, 6:230-42, 2005.
Montagnac et al., "Intracellular trafficking of CD23: differential regulation in humans and mice by both extracellular and intracellular exons," Immunol., 174:5562-72, 2005.
Oh et al., "Reduction of interleukin 8 gene expression in reflux esophagitis and Barrett's esophagus with antireflux surgery," Arch. Surg., 142:554-60, 2007.
Plager et al. "A novel and highly divergent homolog of human eosinophil granule major basic protein," J. Biol. Chem., 274:14464-73, 1999.
Savidge et al., "Enteric glia regulate intestinal barrier function and inflammation via release of S-nitrosoglutathione," Gastroenterology, 132:1344-58, 2007.
Spergel "Eosinophilic oesophagitis and pollen," Clin. Exp. Allergy, 35:1421-2, 2005.
Spergel et al., "The use of skin prick tests and patch tests to identify causative foods in eosinophilic esophagitis," J. Allergy Clin. Immunol., 109:363-8, 2002.
Spergel et al., "Treatment of eosinophilic esophagitis with specific food elimination diet directed by a combination of skin prick and patch tests," Ann. Allergy Asthma Immunol., 95:336-43, 2005.
Spergel, "Eosinophilic esophagitis in adults and children: evidence for a food allergy component in many patients," Curr. Opin. Allergy Clin. Immunol., 7:274-8, 2007.
Stein et al., "Anti-IL-5 (mepolizumab) therapy for eosinophilic esophagitis," J. Allery Clin. Immunol., 118:1312-9, 2006.
Straumann et al., "Cytokine expression in healthy and inflamed mucosa: probing the role of eosinophils in the digestive tract," Inflamm. Bowel Dis., 11:720-6, 2005.
The Merck Index Online, Gelatin, Monograph ID: M5685, Royal Society of Chemistry, 2013.

* cited by examiner

FIGS. 2A-2J
| Design | Description | Overview |
|---|---|---|
| 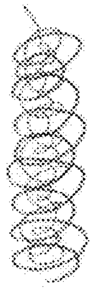 2A. | Layers, dispensing from interior | Superior design: has a hole in center of capsule dispensing string allowing for efficient dispensing |
| 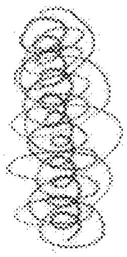 2B. | Layers, dispensing from exterior | Hole in center of capsule dispensing string |
| 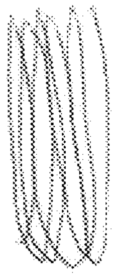 2C. | Longitudinal | |
| 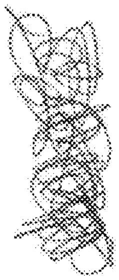 2D. | No configuration | Easy to manufacture |

FIGS. 2A-2J CONTINUED
| | | |
|---|---|---|
| 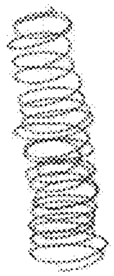 2E. | No layering | Low snag rate |
| 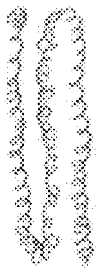 2F. | Thin, tightly bound longitudinal layers | Efficient use of capsule space |
| 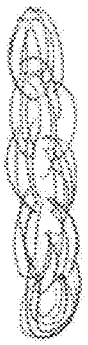 2G. | Twist | |
| 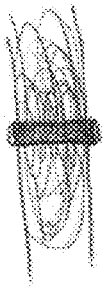 2H. | Interior short spool | Low snag rate but requires extra manufacturing |

FIGS. 2A-2J CONTINUED
| | | |
|---|---|---|
| 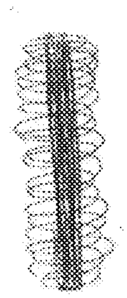 2I. | Interior long spool | Low snag rate but requires extra manufacturing |
| 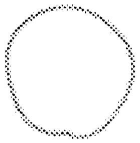 2J. | Circular | Most symmetrical but not as efficient and less likely to use |

B.

A.

DEVICES, METHODS AND SYSTEMS FOR SAMPLING AND ANALYZING THE GASTROINTESTINAL TRACT

PRIORITY

This U.S. Continuation Application claims priority to International Application PCT/US2022/011128 filed Jan. 4, 2022, which claims the benefit of U.S. Provisional Application No. 63/133,712 filed Jan. 4, 2021. Both applications are incorporated herein by reference in their entirety for all purposes.

FIELD

Embodiments of the present invention relate to devices and uses thereof for sampling, analyzing, testing and diagnosing medical disorders or monitoring health status of a subject. In certain embodiments, improved gastrointestinal (GI) sampling devices are disclosed including a line having a proximal segment and a distal segment configured for optimal deployment, reduced discomfort, improved analyte collection of the upper GI tract having reduced cross contamination for analysis, diagnosis and treatment of a subject.

BACKGROUND

Diagnosing health conditions of the gastrointestinal tract such as severe gastroesophageal reflux disease (GERD), eosinophilic gastroenteritis (EGE), food allergic enteropathy (FAE), microbial infections, and inflammatory bowel disease (IBD) is often difficult. In certain cases, non-invasive access to the gastrointestinal (GI) tract is only available through radiographic or stool analysis but these methods fail to provide definitive diagnostic information for many GI disorders.

Currently, endoscopic analysis is used to obtain mucosal sampling for diagnosis and treatment regimens. For certain conditions, such as Crohn's disease, histopathological features can be clearly recognized. For other conditions, such as eosinophilic gastroenteritis and food allergic disorders, histological features are more difficult to assess and there is often overlap with other conditions making it more difficult to diagnose.

There is a need for more efficient, effective and minimally invasive devices for collecting GI tract-associated molecules for improved diagnosis and treatment and monitoring of health conditions.

SUMMARY

Embodiments disclosed herein concern devices and uses for sampling, testing and diagnosing medical disorders or monitoring health status of a subject through GI tract analysis in the subject.

In certain embodiments, improved gastrointestinal (GI) sampling devices are disclosed including a device having an ingestible and optionally, digestible outer capsule, a line or drag material at least partially enclosed with the capsule for deployment in a subject during use, and a weight enclosed within the capsule.

In certain embodiments, the line is optimally configured for deployment from the outer capsule within the GI tract of a subject during use. In some embodiments, the line or drag material can be wound to be configured for optimal enclosure within the outer capsule. In accordance with these embodiments, the line or drag material can be wound to be configured in a layered-loop orientation with a hole in the center, where the loops remain separated from one another and do not overlap and where the proximal end of the line is internally fed for optimal deployment in a subject. In other embodiments, the line or drag material can be wound to be configured in a layered-loop orientation with a hole in the center, where the loops remain separated from one another and do not overlap and where the proximal end of the line is externally fed for optimal deployment in a subject.

In certain embodiments, the line can include a proximal segment and a distal or sampling segment. In certain embodiments, the proximal segment and distal segment form a unitary line, while in other embodiments, the proximal segment and distal segment are operably attached to form the line. For instance, in certain embodiments, an end (e.g., distal end) of the proximal segment is operably attached to an end (e.g., proximal end) of the distal segment. In some embodiments, one end (e.g., the distal end) of the proximal segment can be tapered in order to attach to an end (e.g., the proximal end) of the distal segment; which can be optionally tapered. In certain embodiments, the ends of the proximal and distal segments may be operably attached using an adhesive, thermal bonding, intertwining, weaving, or other suitable affixation method where when deployed remain affiliated with one another.

In some embodiments, the outer capsule may be configured as a two-part capsule including a cap and a base, where the cap and base operably mate to enclose the line and weight within an interior of the operably mated cap and base.

In some embodiments, the cap of the two-part capsule can include a line deployment opening, wherein the proximal end of the line (e.g., the proximal end of the proximal segment) extends through the opening. In accordance with these embodiments, the line can deploy through the opening when provided to a subject in order to capture agents affiliated with the GI tract of a subject.

In some embodiments, the base of the two-part capsule can include a terminal end securement opening, wherein a terminal portion of the distal end of the line (e.g., the terminal distal end of the distal segment) extends over a top surface of the base, along an outer perimeter of the base, and through the terminal end securement opening to thereby extend back into the interior of the base. The portion of the line extending along the outer perimeter of the base can be located between the base and the cap when the cap is operably mated to the base, so as to releasably secure the distal end of the line to the outer capsule. The cap and base can be configured such that the cap extends over the line securement opening when operably mated.

In some embodiments, the outer capsule including a cap and/or a base can be made of but is not limited to, gelatin (e.g. bovine gelatin, vegan gelatin, Kosher, Halal or equivalent material, vegetarian grade gelatin materials), cellulose (e.g. HPMC) Starch (e.g. potato starch), pullulan (e.g. tapioca), polyvinyl alcohol (e.g. copolymer), hemp or other suitable material capable of being degraded, dissolved or passed through the GI system of a subject. In certain embodiments, the outer capsule including a cap and/or base of devices disclosed herein can be a gelatin material or cellulose material. It is contemplated that the material regarding the capsule and or drag material can be made to accommodate any formal requirements depending on the subject to be treated (e.g. dietary restraints and/or religious considerations). In certain embodiments, a capsule of use herein can be about 50% to about 100% bovine pharmaceutical-grade gelatin, Kosher Pareve & Halal Certified, made in a cGMP and FDA-approved facility from BSE-Free or other material to meet specific standards.

In certain embodiments, the weight disclosed herein can be made of, but is not limited to, stainless steel, (e.g. magnetic, austenitic), titanium, ceramic (e.g. alumina, zirconia), glass, cobalt-chromium, gold, silver, tantalum, platinum, other suitable compound, or combination thereof. In certain embodiments, the weight of devices disclosed herein can be stainless steel or titanium.

In accordance with certain embodiments, the outer capsule can be dissolvable, partially dissolvable, or it can pass through the subject's system. In certain embodiments, the line material is malleable in order to configure within the capsule. In some embodiments, the line can be of various lengths for optimal deployment. In some embodiments, a portion of the proximal segment can be pulled out of the capsule prior to swallowing the device or unit and the end of the string or drag material can be attached to the cheek of a subject. In some embodiments, the string or drag material can be attached to the outside of the cheek of the subject. In other embodiments, the string or drag material can be attached to the inside of the cheek of the subject. After a predetermined period of time, the deployed string can be removed from the subject for analysis.

In certain embodiments, the line or drag material is configured for optimal enclosure within the outer capsule and configured for optimal feed from the capsule through the GI tract of a subject. In accordance with these embodiments, the distal segment of the line of the device is capable of feeding through the esophagus, into the stomach and the duodenum of the subject for collecting and/or delivering agents from/to one or more regions of the GI tract. In certain embodiments, the distal segment of the line or drag material includes capture elements that are the same or different along the line or drag material. In other embodiments, capture elements can be positioned along the line, string or drag material directed to the GI section to be analyzed or delivered to when the line, string or drag material is deployed or fully deployed in the subject. In certain embodiments, capture elements can be positioned along the string having capture elements specific for capturing agents in the esophagus that differ from those in the stomach that differ from those in the small and/or large intestine and/or duodenum.

In certain embodiments, the proximal and/or distal segment of the line, drag material or string is made of the same or different materials. In other embodiments, the proximal and distal segments of the line can be made of different materials joined together for optimal sampling of GI tract regions for example, to reduce cross-contamination of collected and delivered agents for more accurate diagnosis, assessment and treatment of the GI tract of the subject. In some embodiments, the proximal and/or distal segment of the line or drag are made of a nylon material. In other embodiments, the line, string or drag material can be made of cotton, rayon, polyester, acrylic, hemp, alpaca, mohair, wool, angora, silk or a combination material.

In some embodiments, the distal segment of the line is made of an absorbent mesh, or textured fiber of a multi-ply configuration. In other embodiments, the distal segment of the line is made of an absorbent mesh, or textured fiber of a 2-5-ply configuration. In other embodiments, the distal segment of the line is made of 2-3-ply material. In some embodiments, the proximal segment of the line can be a single-ply material. In other embodiments, the distal segment of the line can be made of a 2-ply to 3-ply to 4-ply to multiple ply material (e.g. nylon material). In certain embodiments, the proximal segment of the line material can be a single-ply material while the distal segment of the line material can be a 2-, 3-to 4-ply material.

In some embodiments, multi-ply drag, string or line material disclosed herein can be configured to be the same in each ply of the material that makes up the distal segment or each ply can be differently configured in order to maximize sampling of a particular GI region (e.g. capture agent disposition, charge of the line, fingerling inclusions in the line or drag material etc.). In other embodiments, for example, if the distal segment comprises a 3-ply material, each ply can be the same, two of the three be the same or each ply can be differently configured in order to maximize sampling of a GI region or multiple GI regions of a subject. In addition, the proximal segment can be configured similarly to the distal segment containing particular capture agents or can be configured to carry different capture agents.

In certain embodiments, the distal segment of the line can have a failure strength of about 35 N to about 40 N when pulled at about 40-60 mm/min to failure. In other embodiments, the distal segment of the line is capable of absorption of fluid to 1.05, 1.1, 1.15, 1.2, 1.25, 1,3, 1,35, 1.4, 1.45, 1.5 or greater the total weight of the distal segment when it is essentially dry or completely dry. In certain embodiments, fluid absorbed by the distal segment includes fluid obtained from the GI tract of use for analysis of a health condition in a subject.

In some embodiments, capture elements can be provided all along the line or drag material or different capture elements can be positioned along the line or drag material depending on the agents to be captured and the position in the GI tract to be sampled. In accordance with these embodiments, capture elements can be positioned through, for example, molecular immobilization onto the line or drag. In some embodiments, biotin-avidin molecular connector links can be used to attach one or more capture elements. Alternatively, capture elements can be provided in certain methods by changing local surface properties of the line or drag to attract target molecules with counter-properties. In accordance with these embodiments, for example, by making the local surface charge of the line, string, or drag material negative, positively-charged molecules can be attracted to that portion of the line or drag material. Alternatively, by making the local surface charge of the line, string, or drag material positive, negatively-charged molecules can be attracted to that portion of the line or drag material. In other embodiments, by coating local surfaces of the line, string or drag material with functional elements designed to capture targeted proteins or peptides; or by increasing or decreasing the local surface area of the line or string to increase or decrease its capacity to brush against the epithelial and mucosal layers, thereby increasing or decreasing the collection of epithelial cells and mucosa with the surfaces. In certain embodiments, materials selected for the distal segment of the line or drag and/or multi-ply feature of the distal segment of the line or drag material has protrusions (e.g. indentations or raised areas along the drag material) able to brush up against the GI lining and the increased surface area and/or protrusions increase uptake of targeted agents with decreased disruption or integrity of the GI lining compared to standard sampling methods. In some embodiments, the drag, string, or line material of the proximal and/or distal segment surfaces can be inert to reduce interference with testing and to provide improved delivery of targeted agents through the GI tract of a subject. In other embodiments, the drag, string or line material of the proximal and/or distal segment surfaces can be inert to assist with winding configurations of the drag, string or line material as well as unwinding and delivery from the capsule within the GI tract of a subject.

In other embodiments, the line, string or drag material can further include attractant or capture agents capable of binding to agents present in various locations of the GI tract for analysis, diagnosis and analysis and implementation of treatment, as determined by a health professional. In certain embodiments, microbial organisms (e.g. bacteria, fungus, viruses, protozoa) or by-products thereof can be sampled from the GI tract for analysis, diagnosis and proscribed treatment of a subject. In some embodiments, if a GI region is contaminated with a microorganism that releases proteins, by-products and/or or other molecules, the drag or line material can be used to sample for these proteins, by-products or molecules from the microorganism in order to diagnose the condition and treat the condition. In certain embodiments, such sampling can include the mucosal layer of the GI tract in various regions such as the esophagus, stomach or intestines. In other embodiments, devices disclosed herein are designed to capture bile from the bile duct. In accordance with these embodiments, sampling of a subject bile can include sampling from healthy volunteers or subject having a health condition or both for comparison and diagnosis and/or treatment. In some embodiments, bile can be captured by the absorbent material on the distal end of a device for later analysis.

In another embodiment, capture agents can be located along the line, string or drag material. In a particular embodiment, the capture agents can be located in the distal segment of the line, string or drag material. In some embodiments, the capture agent can be any agent capable of binding to an analyte through an interaction or binding that is sufficient to permit the agent to bind and concentrate or attract the analyte out of a heterogeneous mixture of different analytes in a given region of the GI tract. In accordance with these embodiments, the binding interaction can be mediated by an affinity region of the capture agent, by a receptor, by an alloy, by a chemical attractant, by a nucleic acid, by a peptide or other suitable capture agent. In accordance with these embodiments, capture agents can include, but are not limited to antibodies, monoclonal antibodies, antibody fragments (e.g. eosinophil granule or other antibodies), as well as specific agents able to attract inflammatory markers, mucins and/or other agents able to capture mucosa-related markers for later analysis and evaluation.

In some embodiments, devices, methods and uses of the disclosed devices allow for evaluation of inflammation of the GI tract in a subject. In accordance with these embodiments, inflammation of the esophagus of the subject can be assessed, for example, to diagnose a health condition and assess treatment strategy for the subject. In one embodiment, a device of the instant invention can be deployed into GI tract of the esophagus of a subject wherein the distal segment of the device is capable of capturing agents in the subject for diagnosis. The line, string or drag material of the device is removed from the subject's GI tract after a predetermined period of time and the distal segment is analyzed for collection of diagnostic indicators of for example, the esophagus for diagnosis of a health condition such as inflammation, microbial infection or other health condition. It is contemplated herein that a subject can be evaluated before, during or after a prescribed period, on a regular basis and/or before during or after a prescribed treatment period. In some embodiments, a condition of the subject can include, but is not limited to, diseases or conditions of the esophagus or inflammation of the esophagus. For example, the current invention can be used to assess and diagnose gastroesophageal reflux disease (GERD) or complications associated with GERD such as Barrett's esophagus or cancer. In another non-limiting embodiment, the disease may be Eosinophilic Esophagitis (EE). In another embodiment, the condition can be an allergy to one or more foods or components of foods.

In certain embodiments, devices disclosed herein are pharmaceutically acceptable and are further sterilized in order to reduce contamination, etc. In certain embodiments, the device unit which includes all components of the device can be sterilized by ethylene oxide (EO) or other similar agent for sterilization in preparation for use.

In other embodiments, a predetermined period of time for deploying the device within a subject can be any length of time determined by a health professional and/or determined to be optimal for capturing an analyte from the GI tract or delivering an agent to the GI tract of a subject. In accordance with these embodiments, the predetermined time can be from about 15 minutes to about one hour; from about 15 minutes to 2 hours and up to about 12 hours or as needed. In some embodiments, the predetermined period of time for deployment of the string, line or drag material or device can be about 3, 4, 5, 6, 7, 8, 9, 10, 11, 12, 18, 24 or more hours, or any increment thereof.

In other embodiments, after removal of the deployed line, string or drag material from the subject, the distal segment can be analyzed for diagnostic or other health indicators or analyzed to ensure delivery of a specified agent. In some embodiments, a diagnostic indicator or health indicator is absorbed to the line for further analysis when collected from the subject. In other embodiments, one or more capture agents for one or more diagnostic or health indicators can be present on the distal segment of the line or drag material where one or more diagnostic or health indicator can bind to the one or more capture agents for analysis and/or diagnosis. In accordance with these embodiments, the distal segment with or without capture agents can bind to one or more analytes or agents. Analytes and agents can include, but are not limited to, microorganisms (e.g. viruses, bacteria, fungus, protozoans, flagella and the like), cells, cell fragments, proteins, polypeptides (e.g. antigens, enzymes etc.), antibodies or any other captured or harvested agent. Any methods known in the art can be used to analyze agents, analytes, or fluids or other compounds harvested from the GI tract of a subject. In certain embodiments, once the line or drag material is harvested from the subject, it can be stored in a refrigerator or freezer at a predetermined temperature prior to harvesting the analyte or agent, if desired. In other embodiments, the agents, analytes, compounds or other harvested GI resident can be immediately analyzed upon removal of the line, string, or drag material from the subject for rapid assessment and diagnosis as necessary. In certain embodiments, ELISA, cytologic, mass spectrometry, gas chromatography, HPCL, blot (e.g. Western or other), Mesoscale, Licor, PCR, nucleic acid extraction, histology, immunochemical, PCR, microbial culturing, lateral flow assay or other assay can be used to identify the presence or absence of an agent or microbe or byproduct thereof. In certain embodiments, absence or reduced level of an agent in the GI tract can be diagnostic of a condition such as decrease or absence of an enzyme or other health indicator.

In certain embodiments, the one or more diagnostic indicators can be any factor that indicates presence or severity of inflammation of the esophagus or other GI tract region. In some embodiments, the diagnostic indicator can be one or more eosinophil granule protein, including, but not limited to, major basic protein (MBP), an eosinophil cationic protein (ECP), an eosinophil peroxidase (EPO), and an eosinophil-derived neurotoxin (EDN). In some embodiments, the diagnostic indicator can be a cytokine or chemokine, such as eotaxin or other inflammatory marker such as an arachidonic acid product, one or more neurotransmitters such as substance P and bradykinin, an interleukin or otherwise. In another embodiment, the diagnostic indicator can be a cellular infiltrate not normally found in the GI tract being sampled. In yet other embodiments, pH of the GI region can be assessed. In yet another embodiment, the one or more diagnostic indicator can be a marker of an allergic response. In accordance with these embodiments, these agents can include, but are not limited to, IgE, tryptase, histamine, receptor molecules (e.g. FcRI or CD23) or other allergen associated with an allergy. Cellular diagnostic or health indicators contemplated herein can include cellular markers including, but not limited to, peripheral and/or plasma eosinophil counts (e.g. compared to a control not having a condition), mast cells, and other inflammatory markers and/or immune cells associated with a health condition or marker associated with development of one or more health conditions. In other embodiments, diagnostic indicators can include one, two, three, four or more markers.

Definitions

The term "about" as used herein can indicate that a value includes the standard deviation of error for the device or method being employed to determine the value such as +/−10 percent.

The term "assessing" as used herein includes any form of measurement, and includes determining if an element is present or not. The terms "determining," "measuring," "evaluating," "assessing" and "assaying" are used interchangeably and may include quantitative and/or qualitative determinations.

The term "subject" as used herein refers to any member of the animal kingdom, as well as a human.

The terms "treatment," "treating," "treat," and the like as used herein, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-2J represent exemplary configurations of a line or drag material of some embodiments disclosed herein.

DETAILED DESCRIPTION

Figure 1:
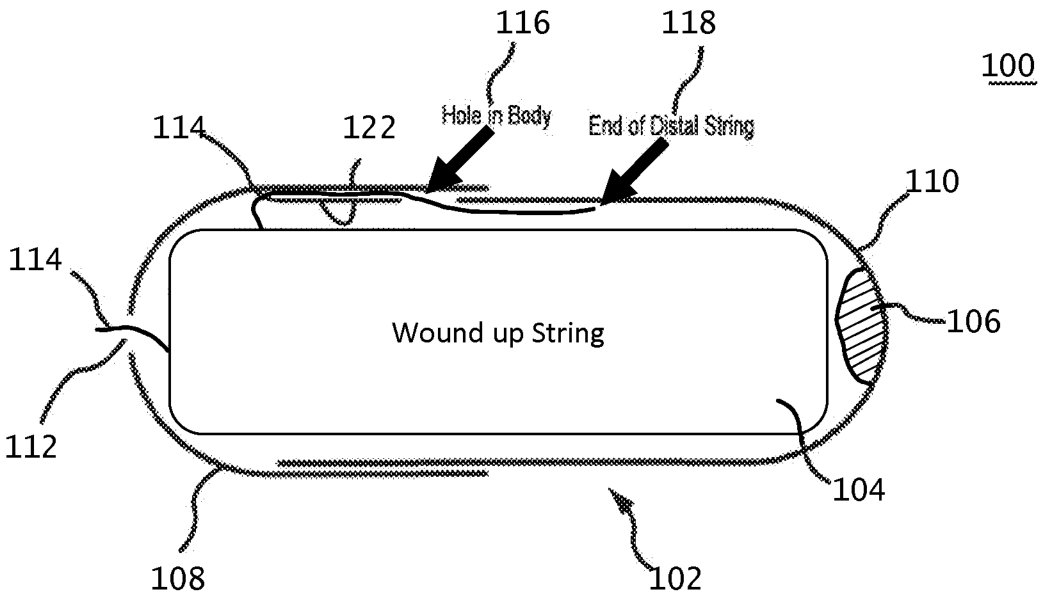
FIG. 1 illustrates a representative device illustrating a distal segment termination to a 2-part capsule, in accordance with certain embodiments disclosed herein.

Embodiments disclosed herein concern devices and uses for sampling and testing and diagnosing medical disorders or monitoring health status of a subject through GI tract analysis in the subject. With reference to FIG. 1, in certain embodiments, improved gastrointestinal (GI) sampling devices are disclosed including a device 100 having an ingestible and optionally, digestible outer capsule 102, a line, string or drag material 104 at least partially enclosed with the capsule for deployment in a subject during use, and a weight 106 enclosed within the capsule.

In certain embodiments, the line can include a proximal segment and a distal or sampling segment (not illustrated). In certain embodiments, the proximal segment and distal segment form a unitary line, while in other embodiments, the proximal segment and distal segment are operably attached to form the line. For instance, in certain embodiments, an end (e.g., distal end) of the proximal segment is operably attached to an end (e.g., proximal end) of the distal segment. In some embodiments, one end (e.g., the distal end) of the proximal segment can be tapered in order to attach to an end (e.g., the proximal end) of the distal segment; which can be optionally tapered. In certain embodiments, the ends of the proximal and distal segments may be operably attached using an adhesive, thermal bonding, intertwining, weaving, or other suitable affixation method.

In some embodiments, the outer capsule 102 may be configured as a two-part capsule including a cap 108 and a base 110, wherein the cap 108 and base 110 operably mate to enclose the line 104 and weight 106 within an interior of the outer capsule 102.

In some embodiments, the cap 108 of the two-part capsule 102 can include a line deployment opening 112, wherein the proximal end 114 of the line 104 (e.g., the proximal end of the proximal segment) extends through the opening 112.

In some embodiments, the base 110 of the two-part capsule 102 can include a terminal end securement opening 116, wherein a portion of the distal end 118 of the line 104 (e.g., the distal end of the distal segment) extends over a top surface 120 of the base 110, along an outer perimeter 122 of the base 110, and through the terminal end securement opening 116 to thereby extend back into the interior of the base 110. The line extending along the outer perimeter of the base may be located between the base and the cap when the cap is operably mated to the base, so as to releasably secure the distal end of the line to the outer capsule. The cap and base may be configured such that the cap extends over the line securement opening when operably mated.

In certain embodiments, the line 104 is optimally configured for enclosure within the outer capsule 102 for deployment from the outer capsule 102 within the GI tract of a subject during use. Any suitable configuration of line that allows for enclosure within the outer capsule together with deployment from the outer capsule may be used in connection with the devices of the disclosure. In certain embodiments, the configurations provide for efficient release from the capsule 102 through the line deployment opening 112. By way of non-limiting example, illustrative winding configurations for optimal enclosure within the outer capsule are shown in FIGS. 2A-2J, and any such configurations may be used in connection with the devices of the disclosure. For instance, as shown in FIG. 2A, the line or drag material can be wound to be configured in a layered-loop orientation with a hole in the center, where the loops remain separated from one another and do not overlap and where the proximal end of the line is internally fed for optimal deployment in a subject. In another embodiment, as shown in FIG. 2B, the line or drag material can be wound to be configured in a layered-loop orientation with a hole in the center, where the loops remain separated from one another and do not overlap and where the proximal end of the line is externally fed for optimal deployment in a subject. Further embodiments of illustrative winding configurations of the line are illustrated in FIG. 2C (longitudinal), FIG. 2D (random), FIG. 2E (no layering of loops), FIG. 2F (thin, tight longitudinal layers), FIG. 2G (twist), FIG. 2H (interior short spool), FIG. 2I (interior long spool), and FIG. 2J (circular).

In some embodiments, the outer capsule including a cap and/or a base can be made of but is not limited to, gelatin (e.g. bovine gelatin, vegan gelatin, Kosher, Halal or equivalent material, vegetarian grade gelatin materials), cellulose (e.g. HPMC) Starch (e.g. potato starch), pullulan (e.g. tapioca), polyvinyl alcohol (e.g. copolymer), hemp or other suitable material capable of being degraded, dissolved or passed through the GI system of a subject. In certain embodiments, the outer capsule including a cap and/or base of devices disclosed herein can be a gelatin material or cellulose material. It is contemplated that the material regarding the capsule and or drag material can be made to accommodate any formal requirements depending on the subject to be treated (e.g. dietary restraints, allergies and/or religious considerations). In certain embodiments, a capsule of use herein can be about 50% up to about 100% bovine pharmaceutical-grade gelatin, Kosher Pareve & Halal Certified, made in a cGMP and FDA-approved facility from BSE-Free or other material to meet specific standards.

In certain embodiments, the weight disclosed herein can be made of, but is not limited to, stainless steel, (e.g. magnetic, austenitic), titanium, ceramic (e.g. alumina, zirconia), glass, cobalt-chromium, gold, silver, tantalum, platinum, other suitable compound, or combination thereof. In certain embodiments, the weight of devices disclosed herein can be stainless steel or titanium.

In accordance with certain embodiments, the outer capsule can be dissolvable, partially dissolvable, or it can pass through the subject's system naturally without issue. In certain embodiments, the line, string or drag material is malleable in order to configure within the capsule. In some embodiments, the line, string or capture material can be of various lengths for optimal deployment. In some embodiments, a portion of the proximal segment can be pulled out of the capsule prior to swallowing the device or unit and the end of the string can be attached to the cheek of the subject. After a predetermined period of time, the string can be removed from the subject for analysis.

In certain embodiments, the line is configured for optimal enclosure within the outer capsule and configured for optimal feed from the capsule through the GI tract of a subject. In accordance with these embodiments, the distal segment of the line of the device is capable of feeding through the esophagus, and into the stomach and the duodenum of the subject for collecting and/or delivering agents from/to one or more regions for analysis. In certain embodiments, the distal segment of the line or drag material includes capture elements that are the same or different along the line or drag material. In other embodiment, capture elements can be positioned along the line or drag material directed to the GI section to be analyzed or delivered to when the line or drag material is fully deployed. In certain embodiments, capture elements can be positioned along the string, line or drag material having capture elements specific for capturing agents in the esophagus that differ from those in the stomach that differ from those in the small and/or large intestine and/or duodenum and/or bile duct.

In other embodiments, the line further comprises attractant or capture agents capable of binding to agents or molecules present in various locations of the GI tract for analysis, diagnosis and analysis and implementation of treatment, as determined by a health professional. In certain embodiments, microbial organisms (e.g. bacteria, fungus, viruses, protozoan) or by-products thereof can be sampled from the GI tract for analysis, diagnosis and proscribed treatment of a subject. In certain embodiments, a pathogenic organism can be detected in the GI tract of the subject for use of diagnosis and treatment of the subject.

In some embodiments, capture elements can be provided all along the line, string or drag material or different capture elements can be positioned along the line, string or drag material depending on the agents to be captured and the position in the GI tract to be sampled. In accordance with these embodiments, capture elements can be positioned through, for example, molecular immobilization onto the line, string or drag material. In some embodiments, biotin-avidin molecular connector links can be used to attach one or more capture elements along the string, line or drag material (e.g. nylon ply material). Alternatively, capture elements can be provided in certain methods by changing local surface properties of the line or drag to attract target molecules with counter-properties. In accordance with these embodiments, for example, by making the local surface charge of the line or drag material negative, positively-charged molecules can be attracted to that portion of the line, string or drag material. Alternatively, by making the local surface charge of the line, string or drag material positive, negatively-charged molecules can be attracted to that portion of the line or drag material. In other embodiments, by coating local surfaces of the line, string or drag with functional elements designed to capture targeted proteins or peptides; or by increasing or decreasing the local surface area of the line or string to increase or decrease its capacity to brush against the epithelial and mucosal layers, thereby increasing or decreasing the collection of epithelial cells and mucosa or mucosal-associated molecules with the surfaces. In certain embodiments, materials selected for the distal segment of the line, string, or drag material and/or multi-ply feature of the distal segment of the line, string or drag material has protrusions able to brush up against the GI lining (e.g. mucosal surfaces) and the increased surface area and/or protrusions increase uptake of targeted agents with decreased disruption or integrity of the GI lining compared to standard sampling methods. In some embodiments, the drag material can be a smooth nylon material with minor projections or protrusions capable of interacting with the mucosal surface by brushing up against the mucosal lining while maintaining its structural integrity with minimal interference in deployment within a subject while absorbing agents within the mucosal lining for later analysis. In accordance with these embodiments, the distal segment of the drag or line material can be made up of nylon where each ply that makes up the line or drag includes the same or different grades of nylon or other suitable material. In some embodiments, mucins can be collected using devices disclosed herein in order to assess a condition of the small and/or large intestinal mucosa. In some embodiments, mucins are indicative a condition of the GI tract of a subject depending on the mucins collected and concentrations found. In some embodiments, conditions disclosed herein can include colitis, Crohn's disease, irritable bowel syndrome (IBS or IBD), allergic reactions to foods, celiac disease, autoimmune conditions, or other agents or the like. In other embodiments, the drag material can be a rougher nylon material with an increased number of projections or protrusions capable of interacting with the mucosal surface by brushing up against the mucosal lining collecting an increased number of GI-associated molecules while maintaining its structural integrity with minimal interference in deployment within a subject while absorbing agents within the mucosal lining for later analysis.

In other embodiments, the line, string or drag material further includes one or more attractants or capture agents capable of binding to agents present in various locations of the GI tract for analysis, diagnosis and analysis and implementation of treatment, as determined by a health professional. In certain embodiments, microbial organisms (e.g. bacteria, fungus, viruses, protozoan) or by-products thereof can be sampled from the GI tract for analysis, diagnosis and proscribed treatment of a subject. In some embodiments, if a GI region is contaminated with a microorganism such as a pathogenic organism or non-native organism that releases proteins, by-products and/or other molecules, the drag, string or line material can be used to sample these proteins, by-products or molecules produced from the microorganism in order to diagnose the condition and/or treat the condition. In certain embodiments, such sampling can include the mucosal layer of the GI tract in various regions such as the esophagus, stomach or intestines.

In another embodiment, capture agents can be located on the line or drag. In certain embodiments, the capture agents can be located in the distal segment of the line. In some embodiments, the capture agent can be any agent capable of binding to an analyte through an interaction or binding that is sufficient to permit the agent to bind and concentrate or attract the analyte out of a heterogeneous mixture of different analytes in a given region of the GI tract. In accordance with these embodiments, the binding interaction can be mediated by an affinity region of the capture agent, by a receptor, by an alloy, by a chemical attractant, by a polynucleotide (e.g. mRNA, DNA, RNA molecule), by a peptide, polypeptide or other suitable capture agent. In accordance with these embodiments, capture agents can include, but are not limited to antibodies, monoclonal antibodies, antibody fragments (e.g. eosinophil granule or other antibodies).

In certain embodiments, the proximal and/or distal segment of the line is made of the same or different materials. In other embodiments, the proximal and distal segments of the line can be made of different materials joined together for optimal sampling of GI tract regions for example, to reduce cross-contamination of collected and delivered agents for more accurate diagnosis, assessment and treatment of the GI tract of the subject. In some embodiments, the proximal and/or distal segment of the line or drag are made of a nylon material. In other embodiments, the line or drag material can be made of cotton, rayon, polyester, acrylic, hemp, alpaca, mohair, wool, angora, silk or a combination material.

In some embodiments, the distal segment of the line is made of an absorbent mesh, or textured fiber of a multi-ply configuration. In other embodiments, the distal segment of the line is made of an absorbent mesh, or textured fiber of a 2-5-ply configuration. In other embodiments, the distal segment of the line is made of 2-3-ply material. In some embodiments, the proximal segment of the line can be a single-ply material. In other embodiments, the distal segment of the line can be made of a 2-ply to 3-ply to 4-ply to multiple ply material (e.g. nylon material). In certain embodiments, the proximal segment of the line material can be a single-ply material while the distal segment of the line material can be a 2-, 3-to 4-ply material.

In some embodiments, multi-ply drag or line material disclosed herein can be configured to be the same in each ply of the material that makes up the distal segment or each ply can be differently configured in order to maximize sampling of a particular GI region (e.g. capture agent disposition, charge of the line, fingerling inclusions or protrusions in the line or drag material etc.). In other embodiments, for example, if the distal segment comprises a 3-ply material, each ply can be the same, two of the three be the same or each ply can be differently configured in order to maximize sampling of a GI region or multiple GI regions of a subject. In addition, the proximal segment can be configured similarly to the distal segment containing particular capture agents or can be configured to carry different capture agents.

In some embodiments, the distal segment of the line or drag material is nylon (e.g. CORDURA Nylon, Nylon 6-6 Fiber, Nylon Industrial Fiber, Nylon Polyamide Fiber, White Dyeable Nylon; Nylon Staple Fibre/Tow). In other embodiments, the distal segment can be a 3-ply, spun, Nylon 9/3 string or other comparable material having highly absorptive equivalents thereof. In certain embodiments, it is contemplated that the nylon or other material used herein can have an absorption of approximately 8-10 times its weight in water or other suitable liquid to increase liquid capture for analysis. In accordance with these embodiments, the distal segment of the line, string or drag material is capable of remaining in the GI tract of a subject and can absorb diagnostic agents, health indicators, microorganisms or by-products thereof or biofluids located in the esophagus, the stomach, bile duct, duodenum, intestines or other region of the GI tract. In some embodiments, the distal segment of the line or drag can be any length determined by a health professional. In some embodiments, the distal segment can be about 500 to about 900 mm or about 600 to about 800 mm or other suitable length (e.g. 775 mm) depending on the subject to be analyzed or the desired GI region to be targeted.

In some embodiments, the proximal segment of the line or drag material can be a single ply, parallel fiber string. In certain embodiments, the proximal segment of the line or drag material can be a single ply segment of Nylon 6/6. In other embodiments, the proximal segment or drag material is selected to be not very absorptive but to be a biocompatible material. In other embodiments, it is desirable for the line or drag proximal segment when wound up to not take up very much space in the capsule and wind and unwind as efficiently as possible. In some embodiments, the proximal segment of the line or drag material can be about 250 to about 400 mm; or about 300 to about 400 mm or about 356 mm. In some embodiments, the proximal segment of the line or drag material is adhered to a distal segment and a loop is created at the opposite end of the proximal segment of the adhered portion of the proximal segment. It is contemplated that the looped end can be used to attach to the subject either inside or outside of the subject's mouth. In some embodiments, the distal and proximal interfaces are designed to have reduced interference when released from the capsule. In other embodiments, the materials used for the drag or line material are inert. In other embodiments, the drag or line material comprises protrusions that extend out from the material with minimal interference of deployment.

In some embodiments, the distal segment of the line or drag material can be a spun material. In some embodiments, unlike the proximal segment described herein, the distal segment of the line or drag has high absorptive properties. In certain embodiments, the distal segment is a 3-ply material (e.g. Nylon 9/3 string). In some embodiments, the drag or line material absorptive quality can absorb from about 5 to about 15 times; to about 8 to about 12 times; to about 8 to about 10 times its weight in water. In some embodiments, the distal segment of the line or drag material can be about 500 to about 900 mm; or about 500 to about 800 mm; or about 600 to about 800 mm or about 775 mm in length when part of the full-length drag material having a proximal and distal segment.

In some embodiments, an adhesive can be used for adhering the proximal segment to the distal segment of the line, string or drag material. In some embodiments, the adhesive can be a silicone or other biocompatible adhesive. In other embodiments, adhesive can be used to form a loop in the proximal segment. In some embodiments, strength of the adhesive can be important for adhering the proximal segment to the distal segment of the line or drag material. For example, strength of the interface of the segments should be strong enough to withstand the tension created by removing the string from the subject's GI tract during normal use and/or to withstand the tension created if the device drag, string or line material does not deploy correctly and it needs to be removed from the subject. This could be the case when the capsule is not detached from the drag or line when the device is deployed in a subject creating more tension than just the string being removed by itself. In certain embodiments, adhesives of use herein can withstand a tension of about ION to about 24N or greater.

In certain embodiments, the distal segment of the line can have a failure strength of about 35 N to about 40 N when pulled at about 40-60 mm/min to failure. In other embodiments, the distal segment of the line is capable of absorption to 1.05, 1.1, 1.15, 1.2, 1.25, 1,3, 1,35, 1.4, 1.45, 1.5 or greater the total weight of the distal segment when it is essentially dry or completely dry.

In some embodiments, the capsule including a cap and/or a base can be made of but is not limited to, gelatin, cellulose (e.g. HPMC) Starch (e.g. potato starch), pullulan (e.g. tapioca), polyvinyl alcohol (e.g. copolymer), hemp or other suitable material capable of being degraded, dissolved or passed through the GI system of a subject. In certain embodiments, the capsule including a cap and/or base of devices disclosed herein can be a gelatin material or cellulose material. In certain embodiments, the 2-part capsule or capsule of the device can be made of a non-vegetarian gelatin. In some embodiments, for ease of manufacturing, the capsule can be a single size for any subject. In other embodiments, for sample subject such as livestock or other animals, a capsule and other components of the device can be adjusted for optimal sampling of any animal or mammal such as a horse, cow, dog, cat or other animal for diagnostic purposes or to assess health of the animal.

In other embodiments, holes can be introduced to the capsule (e.g. by drilling or punch) in order to, for example, facilitate assembly and function of the assembly of the capsule. In certain embodiments, one or more holes can be generated (e.g. drilled) in the end of a capsule cap and one or more holes can be generated in the capsule base or body. In certain embodiments, one or more holes can be introduced to the side of the base or body of the capsule. In some embodiment, the diameter of the one or more holes is about 0.5 mm to about 3 mm. In other embodiments, the diameter of the one or more holes is about 1.5 mm to about 2.5 mm or about 2.0 mm in diameter. In some embodiments, a hole placed in the end of the capsule should be relatively smooth with little to no cracks around the entire diameter. In other embodiments, a holed placed in the base or body of the capsule, such as the side does not need to be relatively smooth, but has little to no cracks around the diameter of the hole.

In certain embodiments, the weight of devices disclosed herein can be made of, but is not limited to, stainless steel, (e.g. magnetic, austenitic), titanium, ceramic (e.g. alumina, zirconia), glass, cobalt-chromium, gold, silver, tantalum, platinum, other suitable compound, or combination thereof. In certain embodiments, the weight of devices disclosed herein can be stainless steel or titanium. In some embodiments, the weight can be a stainless-steel ball. In other embodiments, the stainless-steel ball can be made of 316 grade stainless steel. In accordance with these embodiments, these balls can be treated to remove any contaminants or debris. In certain embodiments, the size of the balls can be about $1/16^{th}$ to about $3/8^{th}$ of an inch (e.g. 2 to about 8 mm) In other embodiments, the size of the balls can be about 3/16 of an inch (about 4 to about 5 mm) in diameter so that they fit into the bottom of the base or body of the capsule.

In certain embodiment, the device herein can include approximately six different components disclosed herein. In accordance with these embodiments, a proximal and distal segment can be adhered together using an adhesive and a loop can be made on the un-adhered proximal segment end. Once the adhesive cures, the drag or line can be wound up and inserted into the base of a capsule on top of the weight positioned at the end of the capsule (e.g. gelatin capsule or other capsule). To adhere the proximal and distal strings together, both strings can be fanned out when an adhesive agent is applied so that strands of the proximal and distal segments can be intertwined together during the adhesion process. It is noted that simply overlapping the strings similar to a lap solder joint cannot meet the strength requirement of this interface. Intertwining the proximal with the distal segment ends increases the strength of the joint between the two segments allowing for the weight to be attached without undoing the ends.

In other embodiments, adhering the weight to the inner capsule by an adhesive agent creates a non-sterile surface that can expose a subject to the unsterile surface because the weight remains within the capsule during sterilization. In some embodiments, the weight does not include an adhesive so that it is freely sterilizable. In some embodiments, the line or drag can be wound in a specific configuration to accommodate the deployment and detachment of the line from the capsule. (See FIGS. 2A-2J) In other embodiments, the line, string or drag can be configured where winding is started with the proximal string. The proximal string can be wound in multiple layers. When wound, in some embodiments, 2-5 or 3-4 layers of proximal segments remain after completing this part of the winding process. In other embodiments, an interface between the proximal and distal segments of the string can be wrapped around the outside of the wound proximal segment. In certain embodiments, this positioning can facilitate proximal segment deployment inside of the interface, and permit the interface to expand to the exterior of the capsule without interfering with the deploying the distal portion of the line or drag material. In some embodiments, the distal segment of the line or drag can be wound. In accordance with these embodiments, the distal segment of the line or drag material can be wound side by side and then back over itself from about 2 to about 4½ times or about 3½ times. It is noted that this winding configuration provided a consistently low deployment force value. Further, in certain embodiments, this winding configuration was designed to provide reduced interference when the line or drag is in the process of deploying from the capsule. In some embodiments, the proximal segment winding and proximal/distal segment interface can create issues with deployment of the line or drag material. In accordance with these embodiments, the interface between the proximal and distal segments can be intertwined to reduce separation while providing minimum deployment interference. In certain embodiments, adhesives can interfere with deploying of the string in a smooth, unobstructed and low-force manner and need to be carefully titrated to ensure smooth pull-out. Similarly, a knot can also interfere with easily removing the string from the capsule. In certain embodiments, adhesive agents can be used to join the segments while minimizing interference by applying only what is needed to join the segments without any excess adhesive agent. In certain embodiments, the distal segment winding can be wound in a configuration sufficient to be placed within the base or body of a capsule and consistently deployed.

In some embodiments, the weight of GI devices disclosed herein (e.g. weighted ball) can include one or more of the following features, can be made of a porous material; can contain surface modifications; can be tethered to small sections of the line or drag material; can contain active elements such as sensing elements (e.g. pH, temperature, pressure), can include a visual feature (e.g. camera or scope); can also include an embedded power such as a battery or radio-frequency antenna to receive power through remote telemetry or a combination of these features. In certain embodiments, the weight can be a stainless steel ball having protrusions or a rough or raised surface for capturing agents. In some embodiments, weights of the devices disclosed herein can be collected from a subject excrement, bowel movement or the like and analyzed for captured mucosally-located agents or other agents. In certain embodiments, the weight (e.g. ball) can be positioned at the extreme distal end of the distal segment and adhered to the distal line or drag material by press fit or by dissolvable adhesive or the like. In some embodiments, wax such as bee's wax are not used to adhere the weight to the distal segment of the line or drag to reduce interference and in order to ensure the weight has been disassociated from the line or drag material and/or excreted. In certain embodiments, MRIs or other diagnostic tools can be used once the weight has exited the subject. In accordance with these embodiments, the weight of the instantly disclosed devices can be used for additional sampling while avoiding excrement contamination based on materials used and configurations of the weight to the drag or line material. In accordance with these embodiments, upper and lower GI sampling is possible using single devices disclosed herein. For example, sampling proximal and distal segments as well as analyzing the weighted component that is excreted from the subject after exposure to the lower GI tract (e.g. lower small and large intestinal mucosal regions) and rectum of a subject.

Figure 3A:
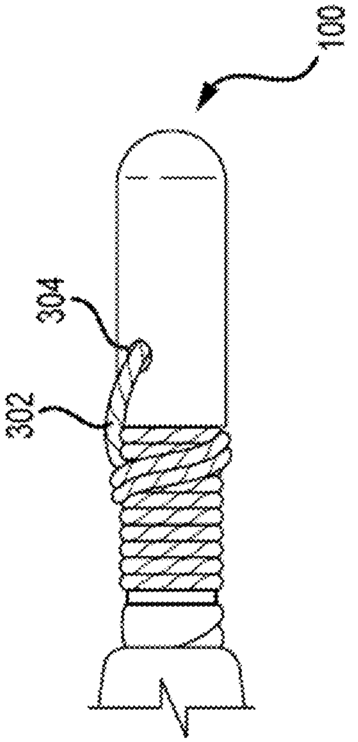
FIGS. 3A and 3B illustrate exemplary aspects of methods for threading the line, string or drag material distal segment termination end of an exemplary device of the disclosure.
Figure 3B:
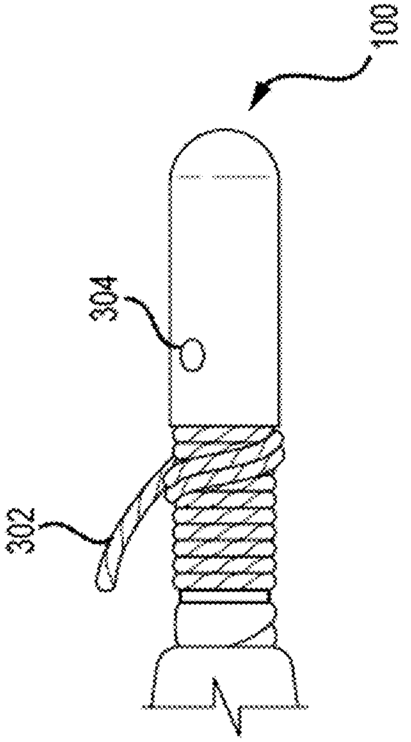

In other embodiments, once the line or drag has been wound a capsule body or base can be slid over the exterior of the string. While sliding the capsule body over the line or drag material, the end of the distal segment can be positioned into the hole of the capsule body (See for example FIGS. 3A and 3B). In some embodiments, this positioning of the distal segment permits the end of the line or drag to be sandwiched between the capsule cap and body when the cap is placed over the open end of the capsule body. In some embodiments, about 2 to about 8 mm of the end of the drag or line is contained within the base secured by the cap of the capsule as depicted in FIGS. 1 and 3A and 3B. In some embodiments, the assembled device can be sealed in pouch (e.g. a Tyvek/poly peel pouch that is 3×4 inches in size), a pouch that is permeable to sterilization (e.g. by ethylene oxide gas).

In other embodiments, devices disclosed herein permit evaluation of inflammation of the GI tract in a subject. In accordance with these embodiments, inflammation of the esophagus of the subject can be assessed, for example, to diagnose a health condition and assess treatment strategy for the subject. In one embodiment, a device of the instant invention can be deployed into GI tract of the esophagus of a subject wherein the distal segment of the device is capable of capturing agents in the subject for diagnosis. The line of the device is removed from the subject's GI tract after a predetermined period of time and the distal segment is analyzed for collection of diagnostic indicators of for example, the esophagus for diagnosis of a health condition such as inflammation, infection or other condition. It is contemplated herein that a subject can be evaluated before, during or after a prescribed period, on a regular basis and/or before during or after a prescribed treatment period. In some embodiments, a condition of the subject can include, but is not limited to, disease of the esophagus may comprise inflammation of the esophagus. For example, the current invention may be used to assess and diagnose gastroesophageal reflux disease (GERD) or complications associated with GERD such as Barrett's esophagus or cancer. In another non-limiting embodiment, the disease may be Eosinophilic Esophagitis (EE). In another embodiment, the condition may be an allergy to one or more foods or components of foods.

In certain embodiments, devices disclosed herein are pharmaceutically acceptable and are further sterilized in order to reduce contamination, prepare for delivery to a subject and other considerations. In certain embodiments, the device unit which includes all components of the device to be introduced to a subject can be sterilized by ethylene oxide (EO) or other similar agent for sterilization without affecting integrity of the device or device components.

Kits are contemplated for devices and other materials disclosed herein. In certain embodiments, each device can be placed in a pouch for delivery in a kit. In some embodiments, a peel pouch can be used to contain devices disclosed herein. In other embodiments, a device assembly disclosed herein can packaged in a combination of Tyvek 1073B and Polyester. In some embodiments, a pouch can contain the device or several pouches in a kit can each contain a single device. In some embodiments, the device has been sterilized and stored in a sealed pouch. In accordance with these embodiments, a pouch can be about 6 mm by about 12 mm or more. In some embodiments, a pouch can be pre sealed on three sides of the pouch. One end of the pouch can further include a chevron that allows the pouch to be opened easier by the user. The fourth side can be sealed once the device has been placed into the pouch. In accordance with these embodiments, the seal on the fourth side can be one that is not designed to be easily peeled but can be peeled. Pouches contemplated herein can be designed to provide a sterile barrier. The other three sides can be sealed and can be pre-made and pre-sealed providing a sterile barrier and be easily peel-able.

In some embodiments, kits contemplated herein can include one or more devices for deployment in a subject. In certain embodiments, kits can include a home kit or a kit for use by medical professionals. In some embodiments, kits can include instructions on how to use the devices disclosed therein and/or instructions for testing and/or sampling and analyzing captured agents, mucosa, pH, microbiome, specific proteins, polypeptides, microorganisms or agents related thereto captured by the device. In certain embodiments, instructions and/or scoring of a single or multiply ply drag material can be included in order to diagnose and/or treat a subject. In some embodiments, kits can be stored for prolonged periods at room temperature, by refrigeration or in a freezer for later use.

In certain embodiments, a predetermined period of time for deploying the device within a subject can be any length of time determined by a health professional and/or determined to be optimal for capturing an analyte from the GI tract or delivering an agent to the GI tract of a subject. In accordance with these embodiments, the predetermined time can be from about 15 minutes to about one hour; from about 15 minutes to 2 hours and up to about 12 hours or as needed. In some embodiments, the predetermined period of time can be about 3, 4, 5, 6, 7, 8, 9, 10, 11, 12, 18, 24 or more hours, or any increment thereof.

In other embodiments, after removal of the deployed line or drag material from the subject, the distal segment can be analyzed for diagnostic or other health indicators or analyzed to ensure delivery of a specified agent. In some embodiments, a diagnostic indicator or health indicator is absorbed to the line for further analysis when collected from the subject. In other embodiments, one or more capture agents for one or more diagnostic or health indicators can be present on the distal segment of the line or drag material where one or more diagnostic or health indicator can bind to the one or more capture agents for analysis and/or diagnosis. In accordance with these embodiments, the distal segment with or without capture agents can bind to one or more analyte or agent. Analytes and agents can include, but are not limited to, microorganisms (e.g. viruses, bacteria, fungus, protozoans, flagella and the like), cells, cell fragments, proteins, polypeptides (e.g. antigens, enzymes etc.), antibodies or any other captured or harvested agent. Any methods known in the art can be used to analyze agents, analytes, or fluids or other compounds harvested from the GI tract of a subject. In certain embodiments, once the line or drag material is harvested from the subject, it can be stored in a refrigerator or freezer at a predetermined temperature prior to harvesting the analyte or agent. In other embodiments, the agents, analytes, compounds or other harvested GI resident can be immediately analyzed upon removal of the line or drag material from the subject for rapid assessment and diagnosis as necessary. In certain embodiments, ELISA, cytologic, mass spectrometry, gas chromatography, HPCL, blot (e.g. Western or other), Mesoscale, Licor, PCR, nucleic acid extraction, histology, immunochemical, microbial culturing, lateral flow assay or other assay can be used to identify the presence or absence of an agent. In certain embodiments, absence of an agent in the GI tract can be diagnostic of a condition such as reduced or absence of an enzyme, reduction or absence of natural flora or microbiome indicator or other health indicator.

In certain embodiments, the one or more diagnostic indicators can be any factor that indicates presence or severity of inflammation of the esophagus or other GI tract region. In some embodiments, the diagnostic indicator can be one or more eosinophil granule protein, including, but not limited to, major basic protein (MBP), an eosinophil cationic protein (ECP), an eosinophil peroxidase (EPO), and an eosinophil-derived neurotoxin (EDN). In some embodiments, the diagnostic indicator can be a cytokine or chemokine, such as eotaxin or other inflammatory marker such as an arachidonic acid product, one or more neurotransmitters such as substance P and bradykinin, an interleukin or otherwise. In another embodiment, the diagnostic indicator can be a cellular infiltrate not normally found in the GI tract being sampled. In yet other embodiments, pH of the GI region can be assessed in order to diagnose one or more conditions. In yet another embodiment, the one or more diagnostic indicator can be a marker of an allergic response. In accordance with these embodiments, these agents can include, but are not limited to, IgE, tryptase, histamine, receptor molecules (e.g. FcRI or CD23) or other allergen associated with an allergy. Cellular diagnostic or health indicators contemplated herein can include cellular markers including, but not limited to, peripheral and/or plasma eosinophil counts (e.g. compared to a control not having a condition), mast cells, and other inflammatory and/or immune cells associated with a health condition or marker associated with development of one or more health conditions. In other embodiments, diagnostic indicators of a condition can include one, two, three, four or more markers related to a health condition or more than one health condition.

In some embodiments, captured agents or analytes can be used to diagnose a disease or condition of the upper GI tract of a subject. Evaluation can include assessment for the presence or absence of an indicator that allows for diagnosis of a disease or condition. For example, if a sample demonstrates evidence of an inflammatory reaction or inflammatory condition (e.g. presence of proinflammatory cytokines), this can indicate the presence of Eosinophilic Esophagitis (EE). Alternatively, the level or concentration of an indicator can be evaluated to either diagnose or evaluate the level or severity of a disease or a condition or treatment regimen. For example, increased levels of eosinophil granule proteins in a sample compared to a control sample can indicate the presence of EE. In other embodiments, increases in pro-inflammatory cytokine expression or activity, such as increases in IL-6 and/or IL-8 compared to a control sample can be linked to the presence of GERD. In certain embodiments, indicators collected from the GI tract using devices disclosed herein can include, but are not limited to, e-cadherin for detection of GERD or other associated conditions; biomarkers for identifying presence of Crohn's disease or other related inflammatory bowel conditions, biomarkers for identifying presence of Colitis or other related conditions; biomarkers for identifying presence of Intestinal Bowel Disease (IBD) or other related conditions; biomarkers or indicators of infectious agents, for example *Helicobacter pylori* (*H. pylori*). *E. coli*, esophageal candidiasis or other bacterial infections or viral infectious agents.

In one embodiment, devices and methods for measuring esophageal inflammation including deploying a device into the GI tract of a subject, removing the device after a predetermined period of time, analyzing the device for a diagnostic indicator of esophageal inflammation, and evaluating the diagnostic indicator to diagnose esophageal inflammation are described. In another embodiment, devices and methods of use thereof can further include quantifying the diagnostic indicator or other agent. In accordance with these methods, quantification can be performed by any method known to those of skill in the art. In certain embodiments, the quantification can be performed by ELISA. In another embodiment, the quantification of captured indicators can be performed by Mesoscale. In other embodiments, treatment of the disease or condition can be applied based on analysis of one or more captured agents, indicators or pH levels of a sample obtained by devices disclosed herein. In addition, treatment regimens can be monitored and adjusted as necessary by sampling the GI tract of a subject, before, during and after a prescribed treatment regimen.

In some embodiments, diagnostic indicator or captured agent can be any agent or factor that indicates the presence or severity of infection, inflammation and/or immunologic disorder or other health condition of the GI tract. In some embodiments, the captured agent can be an eosinophil granule protein, including major basic protein (MBP), an eosinophil cationic protein (ECP), an eosinophil peroxidase (EPO), or an eosinophil-derived neurotoxin (EDN). In some embodiments, the diagnostic indicator is a cytokine or chemokine, such as eotaxin. In another embodiment, the diagnostic indicator is a cellular infiltrate or pH. In yet another embodiment, the diagnostic indicator is a marker of an allergic response, such as IgE, tryptase, receptor molecules (for example, FcRI or CD23) or an allergen. Other inflammatory markers that can be examined can include, for example, arachidonic acid products and neurotransmitters such as substance P and bradykinin. Other diagnostic indicators include peripheral and plasma eosinophil counts, mast cells, including leukotrienes. In other aspects, diagnostic indicators can include one, two or more markers related to a health condition when present, reduced or increased.

In some embodiments, use of the device in methods disclosed herein provide for minimally invasive method for assessing and diagnosing a disease of the esophagus. In some embodiments, distinguishing between GERD and EE in a subject can be determined using devices and methods disclosed herein.

Other than use of devices disclosed herein to capture and analyze agents found in different upper GI compartments, some embodiments disclosed herein concern delivery of an agent such as a pharmaceutical or biological agent on a device line, string or drag material to an upper GI tract of a subject to treat or ameliorate a condition. It is contemplated that any biological agent or chemical can be associated with the line, string or drag material of devices disclosed herein through interactive agents such as biotin-avidin or similar molecules or by charge attraction. In other embodiments, delivery of agents to the GI tract can be more effectively delivered to a particular GI tract location such as the esophagus, stomach, upper intestine, mucosal membranes thereof, etc.

In other embodiments, devices disclosed herein can be designed to capture bile from the bile duct. In accordance with these embodiments, sampling of a subject bile can include sampling from healthy volunteers or subject having a health condition or both for comparison and diagnosis and/or treatment. In accordance with these embodiments, sampling of bile can be used to diagnose conditions associated with bile changes and compare these to a healthy adult or assess presence of agents that are indicative of a condition for example, changes in bile pH, coloration or the like. In some embodiments, assessing the bile of a subject can be used in pharmaceutical clinical trial studies such as Absorption, Distribution, Metabolism, Excretion (ADME) studies, evaluation of drug-drug interaction studies, or other studies regarding identification of target markers, indicative of drug tolerance and of drug efficacy or other analysis.

In some embodiments, a bound-captured agent can refer to one or more agents that are bound to the distal segment of the line, string or drag material for analysis by a healthcare professional or other. In accordance with these embodiments, a bound-captured agent is essentially immobilized on a surface of the drag, string or line material while the device is deployed and for a time after the device is retrieved from the subject.

The predetermined period of time can be various lengths of time. For example, the predetermined time for capturing samples collected from a device disclosed herein can be about 15 minutes to about 12 hours. In some embodiments, the predetermined period of time for capturing samples collected from a device disclosed herein can be about 15 minutes, about 30 minutes, about 45 minutes, about 1, 2, 3, 4, 5, 6, 7, 8, 9, 10, 11, 12, 18, 24 or more hours, or any increment thereof after deploying the device in a subject. In one embodiment, the predetermined period of time can be about 15 minutes. In another embodiment, the predetermined period of time can be about 1 hour. In other embodiments, the predetermined period of time can be about 12 hours after deploying the device.

In some embodiments, after the device is swallowed, the terminal or distal end of the distal segment of the line, string or drag material can reach the lumen of the small intestine. In certain embodiments, GI tract location of the distal segment can be confirmed by the presence or absence of various agents or by a pH indicator associated with the drag or line material or detection of the weight in a subject. Boundaries can be identified for example, by the presence or absence of an agent or analyte and/or between acid and alkaline sections of the drag, string or line material. In some embodiments, after the device is swallowed, a trail of drag, string or line can be left in its path through the esophagus, the stomach and into the duodenum. Within a predetermined period of time, the line, string or drag material is fully deployed and if desired, can remain attached to the capsule as depicted for example, as indicated in FIG. 1. In some embodiments, the capsule dissolves and the weight is excreted through normal processes. In accordance with these embodiments, once the capsule dissolves, the end of the drag, string or line material can be left free in the duodenum for a pre-determined period of time in order to assess one or more health condition of the subject (e.g. 15 minutes to 12 hours).

In some embodiments, after a pre-determined period of time, the drag or line material can be collected or removed from the subject. In accordance with these embodiments, collection or removal of the device from the esophagus can be without the capsule. In some embodiments, the line or drag can be stored for later analysis; for example, by refrigeration or frozen by quick freeze and flat storage (e.g. flash frozen). In other embodiments, the line, string or drag segment can be analyzed soon after or immediately after collection. In other embodiments, the line, string or drag material can be sectioned according to where capture elements were placed or according to the segment of GI tract being sampled. When storing the line, string or drag material post collection, the proximal segment can be partially or fully removed, as desired, for example, to reduce cross contamination. In some embodiments, a captured agent or analyte can be adsorbed in the distal segment of the line. In other embodiments, a captured agent or analyte binds to the outer part of the distal segment. In certain embodiments, captured agents or analytes can be physically scraped off or introduced to a media for part or all of the line for analysis. In yet further embodiments, liquids, secretions or other compositions found in the GI tract can adhere to the distal segment of the line, string or drag material. Presence and analysis of secretions, polypeptides, enzymes, microorganisms and/or cells can be examined by a number of different techniques known in the art. In certain embodiments, presence of inflammatory proteins, cytokines, enzymes, polynucleotides, cells or microorganisms or by-products thereof can be analyzed within the contents removed from the line for analysis and diagnosis and/or treatment regimen. In other embodiments, the line, string or drag material can be analyzed for the level, absence or presence of one or more diagnostic indicators. Analysis can be performed by a number of methods, including but not limited to ELISA, cytology, mass spectrometry, gas chromatography, HPLC, sequence analysis, PCR, Western Blot, Mesoscale, Licor, RNA and DNA extraction, immunohistochemical analysis, and microbial culture and staining. In certain embodiments, diagnostic indicators can be any factor, polypeptide or other agent that indicates the presence or severity of a condition in the subject. In some embodiments, the diagnostic indicator can be an eosinophil granule protein, a cytokine or chemokine, a cellular infiltrate, pH, or a marker of an allergic response. Other diagnostic indicators include, but are not limited to, peripheral and plasma eosinophil counts, mast cells, leukotrienes other immune markers. In other embodiments, a diagnostic indicator can be a microorganism or by-product thereof. In yet other embodiments, captured agents can include markers related to health of a subject such as sampling of the microbiome of a subject. It is contemplated herein that one, two, three, four, five or more or a panel of captured agents or markers can be collected for analysis, health assessment, diagnosis and treatment of a subject's GI tract.

As disclosed herein, eosinophil granule proteins can be obtained and used to analyze a condition of a subject. Eosinophil granule proteins include, but are not limited to, major basic protein (MBP), eosinophil cationic protein (ECP), eosinophil peroxidase (EPO), and eosinophil derived neurotoxin (EDN). These proteins can be secreted upon eosinophil stimulation and induce an inflammatory response. Eosinophil granule proteins can include, but are not limited to, other biologically active products including bacterial permeabilizing protein (BPP) and anti-microbial proteins. Secretion and extracellular deposition of eosinophil granule proteins in tissues affected by inflammatory diseases suggests that MBP, ECP, EPO, and EDN may participate in the pathogenesis of the inflammatory process. Further evidence has demonstrated that the topical application of MBP is associated with tracheal smooth muscle contraction and ion secretion.

In certain embodiments, a subject can be a subject that is part of a clinical trial. In some embodiments, the subject is a participant in clinical trials of new pharmaceutical products such as a study of the Absorption, Distribution, Metabolism, and Excretion (ADME) associated with a new pharmaceutical agent. In accordance with these embodiments, a pharmaceutical agent can be tested on a subject and devices disclosed herein can be used to obtain samples from the subject for analysis.

Other embodiments include, harvesting and analyzing the presence or absence of cytokines or chemokines from a deployed and collected drag, string or line. In some embodiments, cytokines and/or chemokines can be harvested and analyzed from a deployed and collected drag, string or line material for assessment of a health condition in a subject. In certain embodiments, cytokines can include, but are not limited to, interleukins. Cytokines can include, but are not limited to interleukin-1alpha (IL-1α), IL-13, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-32) and interferons. In other embodiments, a diagnostic factor can be a Th2 cytokine (e.g., IL-4, IL-5, IL-13). Chemokines can include, but are not limited to, the eosinophil-specific chemokines eotaxin-1, -2, -3.

Other embodiments include detection of an allergic response marker or indicator of for example, inflammation of a region of the GI tract such as the esophagus. An "allergic response" as used herein can be a disorder in which the host's immune response to a particular antigen is disproportionate to a control not having such a response and that lead to an adverse reaction. Allergies arising from an allergic response can include, but are not limited to, allergies to pollen, ragweed, shellfish, pollutants, any food product, domestic animals, (e.g., cats and dogs), gluten, lactose, B-venom, and other allergens. In certain cases, some allergic responses lead to asthma. In some embodiments, a marker of an allergic response can be, but is not limited to, immunoglobulin E (IgE), tryptase, receptors (FcRI, CD23) or other allergen. Other inflammatory markers that may be captured and analyzed from GI samples can include, but are not limited to, arachidonic acid products and neurotransmitters such as substance P and bradykinin.

In certain embodiments, captured agents using devices disclosed herein can be used to assess, diagnose or monitor a disease or condition of the GI tract of a subject such as the esophagus, stomach, duodenum or other region within accessibility of the deployed line or drag of a device disclosed herein. In accordance with these embodiments, evaluation of a captured agent or indicator can include, but is not limited to, presence, level or absence of sought-after agent or indicator that permits diagnosis of a disease, condition or state of health of a subject. For example, if an agent captured from the esophagus demonstrates presence of inflammation, this can be indicative of eosinophilic esophagitis. Alternatively, the level of an agent or indicator can be indicative of diagnosis or severity of a disease or condition or even be representative of the level of health or prediction for developing a condition not yet present (e.g. microbiome assessment of a healthy subject). In certain embodiments, eosinophil granule protein levels assessed in a subject can indicate the presence of, or risk of developing Eosinophilic Esophagitis (EE). In other embodiments, increases or decreases in cytokines known in the art to be indicators of disease or other health conditions of the GI tract can be isolated on the distal segment of a line or drag material disclosed herein and used for diagnosis and/or treatment of a condition or used to assess the health of a subject. In accordance with these embodiments, as an example, cytokines can include, but are not limited to, IL-6 found in the esophagus of a subject or other GI regions as an indicator of the presence or risk of developing gastroesophageal reflux disease (GERD). In certain embodiments, diagnostic markers or indicators or other agents, can be evaluated to assess the treatment of a disease and whether additional treatment or a change in treatment regimen is needed.

In certain embodiments disclosed herein, the condition can be GERD. GERD includes chronic symptoms or mucosal damage produced by the abnormal reflux in the esophagus. Symptoms can include heartburn, inflammation in the esophageal lining, strictures, dysphagia and chronic chest pain or other symptoms. Treatment of GERD can include food and lifestyle modifications, positional therapy, drug treatment and surgery. Devices disclosed herein can be used to assess, diagnose, and treat GERD or complications associated with GERD such as Barrett's esophagus or cancer of the GI tract associated with GERD.

In other embodiments, disease or conditions disclosed herein can include EE. EE is an eosinophilic gastrointestinal disease (EGID) that accounts for about 50% of dysphagia and food impaction. It has been proposed that food allergy is the underlying etiology of EE. Recent translational studies demonstrated that a skin prick tests (SPTs) is a tool used to identify the triggering food allergens and >90% of patients respond to dietary interventions, humoral (IgE) and/or cell-mediated food allergy. It has been observed that esophageal mast cells are significantly increased in EE compared to normal controls and gastroesophageal reflux disease (GERD). EE is a disorder of the esophagus characterized by esophageal and/or upper gastrointestinal tract symptoms in association with esophageal mucosal biopsy specimens containing high amount of intraepithelial eosinophils within the esophageal squamous epithelium or deeper tissue levels and normal pH monitoring. EE affects males more than females, and the diagnosis is typically made in adults during the third and fourth decades of life, although it may be diagnosed at a later age. In children, the diagnosis is made after infancy and through adolescence with no recognized peak age of onset. Symptoms can include, but are not limited to, chest pain, heartburn, dysphagia, food impaction and a lack of responsiveness to acid reducing medications. Treatment of EE typically includes administering corticosteroids or elemental diet but not typically surgery.

Standard of care for EE patients currently includes esophageal endoscopy with biopsy to determine the numbers of epithelial eosinophils (ltoreq.15/hpf being diagnostic). Since consequences of chronic eosinophilic inflammation in EE can include esophageal remodeling with subsequent esophageal narrowing, trachealization and strictures, therapeutic efforts are typically devoted toward inducing clinical as well as histological remission. While overall relatively safe, esophageal endoscopy entails procedural risks, is expensive, time consuming and is limited to procuring a 3 mm sample. To date, no serological, stool or non-invasive tests have provided durable or reliable results correlating histological evidence of disease progression or remission in EE. The current state of esophageal inflammation in subjects with EE is assessed using an invasive endoscopy.

In certain embodiments, devices disclosed herein can be used to assess EE presence or severity in a subject. In other embodiments, devices disclosed herein can be used for continuous treatment and monitoring as necessary using collection of agents or diagnostic markers identified on the distal segment of the line or drag material in order to assess EE in the subject.

In some embodiments, devices disclosed herein can be used to assess food allergic conditions in subjects in a non-invasive or minimally invasive fashion. In accordance with these embodiments, adults or children can be diagnosed and/or monitored for food allergies using devices disclosed herein. It is noted that studies indicate support for a close relationship of EE with food allergic diseases. Further, it is also noted that subjects with EE often associate symptoms following the ingestion of specific foods. Elimination of food triggers can lead to clinicopathological remission in EE. It has been demonstrated that mucosal biopsies from subjects with EE have significantly increased numbers of mucosal mast cells compared to those from subjects with gastroesophageal reflux disease (GERD) or normal subjects, suggesting their participation in the pathogenesis of this disease. In addition, previous work suggests that a subject with eosinophilic gastrointestinal diseases (EGIDs) and food allergy demonstrate increased expression of CD23 on intestinal epithelial cells and in stool samples. While the precise role of CD23 in food allergic responses is not certain, recent studies suggest that the human CD23a isoform participates as a bidirectional transporter of both free IgE and IgE/antigen complexes, and can potentially deliver IgE and its bound allergen across intestinal epithelial cells to induce mast cell activation. These observations provide strong evidence supporting a role of food allergic responses (including those mediated by IgE) in the pathogenesis of EE. In certain embodiments, diagnosis of food allergies in a subject using devices disclosed can be an efficient method with reduced cost and discomfort to the subject. In some embodiments, one or more agents captured by the device disclosed herein can be used to diagnose a subject having a food allergy in order to provide early intervention and reduce the onset of EE or more severe food allergies in the subject.

EE is characterized by symptoms including abdominal pain, regurgitation, feeding intolerance, food impaction and dysphagia. It is noted that esophageal biopsies contain large numbers of intraepithelial eosinophils, often with eosinophil microabscesses and luminal layering. These advanced symptoms of EE are unresponsive to acid blockade, such as proton pump inhibition, but still respond to elimination (or elemental) diets and corticosteroids. EE does not affect the columnar epithelium of the stomach or small intestine. If a subject has persistent symptoms associated with esophageal epithelial eosinophilia and normal gastric and duodenal mucosa, and gastroesophageal reflux (GERD) and other causes of eosinophilia have been ruled out, the diagnosis of EE can be made with confidence. In certain embodiments, devices disclosed herein can be used for deployment in a subject for early and accurate diagnosis of EE. In accordance with these embodiments, diagnostic markers of EE can be captured on devices disclosed herein, including but not limited to, cells, cytokines and other markers. For example, presence of Th1 or Th2-mediated immune response, mast cells (e.g. induction) can be assessed as well as, IgE-mediated responses, absence or presence of eotaxin-3; eosinophil derived granule proteins (Major Basic Protein 1 (MBP1), eosinophil peroxidase (EPX), eosinophil derived neurotoxin (EDN), eosinophil cationic protein (ECP), Charcot Leyden crystal protein (CLC/Galectin-10), presence, absence or level of IL-3, IL-4, IL-5, IL-10, CD23, and other agents. In certain embodiments, using devices disclosed herein, identifying a Th2 phenotype instead of a Th1 phenotype can be indicative of a GI inflammatory condition or GI infection by a microorganism. In certain embodiments, these GI-related conditions can be diagnosed and monitored in a subject using devices and methods of use disclosed herein.

Limitations of state-of-the-art methods including endoscopy with biopsy include, but are not limited to, the issue that these methods provide an assessment of <0.001% of the total esophageal surface area. Endoscopy is costly and often is not covered by insurance companies when repeated as described above. Other proposed methods to analyze the esophageal mucosa include monitoring symptoms, radiological studies, and serum or stool analyses which are also limited. To date, no serological or stool analysis has provided reliable and durable findings that correlate with and are consistently predictive of histological evidence of disease remission or progression. These findings indicate that a minimally invasive, inexpensive, safe, reliable and accurate method for direct measurement of GI tract state is needed for diagnosis, treatment and monitoring of conditions disclosed herein.

In some embodiments, devices disclosed herein can be used as a simple, cost-effective and reliable device for diagnosis or assessment of GI tract health of a subject. In some embodiments, devices disclosed herein include a proximal and distal segment linked together using intertwined silicone adhered ends for improved recovery of the device from a subject. In other embodiments, winding of the line or drag has been designed for internal or external feed with the remaining line or drag material looped for optimal deployment. In certain embodiments, a weight can be positioned within a two-part capsule away from the line for reliable transport within the GI tract of a subject. In other embodiments, the devices disclosed herein can be sterilized within a pouch where the entire device including the weight can be sterilized for storage and use with reduced concern for contamination. In some embodiments, devices sterilized by compositions and methods disclosed herein can be stored for a few days, a few weeks, a few months, several months or years. In some embodiments, the device proximal segment includes a one-ply nylon while the device distal segment includes a three-ply nylon where the proximal segment nylon has reduced absorption and the distal nylon has increased absorption. In certain embodiments, the proximal and distal segments are tapered towards the joining ends. In some embodiments, adhesion of the proximal and distal segment line components can include a silicone adhesion agent; optionally where the proximal and distal segment ends are intertwined and adhered to one another for improved resistance to separation when deployed and/or collected from a subject.

In accordance with these embodiments, the line, string or drag material can be wound, e.g., as depicted in FIG. 2A or FIG. 2B and a gelatinous capsule base placed over the wound line, string or drag material. In other embodiments, the terminal distal end of the distal segment of the drag, string or line can be positioned between the cap and base of the capsule once the line or drag is positioned within the base of the capsule. In some embodiments, the weight can be positioned away from the line, string or drag exit (e.g. away from the hole in cap and/or side of the device) for reduced interference with the deployment of the line or drag. In some embodiments, the weight can be a ball (e.g. steel). In other embodiments, the proximal segment of the line or drag remains essentially in the mouth or buccal cavity of the subject secured to the cheek or secured outside of the mouth of the subject. In other embodiments, the distal segment of the line or drag can be deployed and remain for a predetermined period of time in the GI tract including, for example, the esophagus, stomach, duodenum, upper small intestinal region, etc. of the subject.

In some embodiments, the capsule is made of a dissolvable material that dissolves once deployed in the subject or after a period of time and the terminal distal end of the distal segment is freed from the capsule remaining in the subject's duodenum or small intestine. At a predetermined period of time, the line or drag material can be removed from the GI tract of the subject by pulling at a predetermined pace to provide for optimal collection of captured agents and/or indicators and/or delivery of therapeutics. Once collected, in certain embodiments, the distal segment of the line, string or drag material can be analyzed for the presence, absence or level of an agent or diagnostic indicator or combinations thereof.

In some embodiments, benefits of the device disclosed herein include, but are not limited to, ease of use—no preparation/anesthesia required, inexpensive, improved versatility in assessing the GI tract conditions of a subject, improved adhesion strength, improved safety in administration and use by pre-sterilization of the device, and/or improved deployment by improved winding, reduced snagging and delivery.

Various biochemical and molecular biology methods referred to herein are well known in the art and are contemplated of use herein.

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Features of devices disclosed in these examples include an ingestible capsule which contains a stainless-steel weighted ball and a bimodal string (proximal and distal portions). As the capsule is swallowed by a patient, the string, which is secured externally to the patient on the proximal end, is deployed along the gastroesophageal tract. After a relatively short period of time in the stomach, the string separates from the capsule, the stainless steel ball passes through the GI tract for natural expulsion by the body, and the deployed string collects bio-fluids such as esophageal fluids, cells and proteins. After a period of time, the string is retracted out of the esophagus and the bio-fluids that have been adsorbed and entrapped in the string are analyzed.

Some Functions: capsules disclosed herein are intended to be a biological sample transport device that gathers a sample or delivers an agent to a patient's GI tract for diagnosis and/or treatment. The capsule does this by deploying a string down the esophagus of the patient. This string has an absorptive quality that allows the string to absorb fluids from the esophagus once deployed. Once the capsule has been swallowed by the patient, the looped end of the proximal string is taped to the check of the patient using for example, a Tegaderm dressing tape. This allows the patient to relax and not have to hold the end of the proximal string during the entire swallowing and deployment process.

Components

Gelatin Capsule

The Gelatin Capsule is made of a non-vegetarian or vegetarian gelatin. It is a standard #1 size capsule. During the assembly process, two holes are drilled into the capsule to facilitate assembly and function of the assembly. One hole is drilled in the end of the capsule cap and one in the side of body of the capsule. These holes are both approximately 2.0 mm in diameter. The hole in the end of the capsule should be smooth and there should be no cracks around the entire diameter. The hole in the side of the capsule does not need to be smooth, but does need to not be cracked around the diameter of the hole.

Proximal String

The proximal string is a single ply, parallel fiber string made of Nylon 6/6. This string was chosen for the proximal string because it is not very absorptive and Nylon is known to be a biocompatible material. Also, this parallel fiber string, when wound up, does not take up very much space in the capsule. This string is cut to a length of approximately 356 mm before being adhered to the distal string and a loop is made at the opposite end of the proximal string.

Distal String

In this example, the distal string is a three ply, spun, Nylon 9/3 string. This string is very absorptive. Based on absorption testing done in the past, this string absorbs approximately 8-10 times its weight in water. This portion of the string is intended to sit in the patient's esophagus and collect the biofluids. The distal string is cut to a length of approximately 775 mm.

Silicone Adhesive

Exemplary silicone adhesive is used to adhere the two types of string together as well as create the loop in the end of the proximal string. The strength of the adhesive is critical for the strength of the interface between the two types of string. However, it is not critical for the strength of the loop. The strength of the interface is required to be strong enough to withstand the tension created by removing the string from the patient's esophagus during normal use. But, also is intended to withstand the tension created if the capsule does not deploy correctly and needs to be pulled from the subject prematurely. This means that the capsule could still be attached to the end of the string creating more tension than just the string being removed by itself. The expected tension was less than 10 N during the previous project. The minimum strength allowed during testing is 23 N. This allows a safety factor greater than 2 for this application.

Stainless Steel Ball

The stainless-steel (SS) ball is made of 316 grade stainless steel. These balls are passivated to remove any contaminants that could be present on the exterior of the material. They are 3/16 of an inch in diameter so that they fit into the bottom of the body of the gelatin capsule. The stainless-steel ball is used in the assembly to help gravity pull the capsule down the GI tract during the procedure.

Peel Pouch

The exemplary peel pouch that the capsule assembly is packaged in is a combination of Tyvek 1073B and Polyester. The pouch is 3 inches by 4 inches and is pre-sealed on three sides of the pouch. One end of the pouch includes a chevron that allows the pouch to be opened easier by the user. The fourth side is intended to be sealed once the capsule assembly has been placed into the pouch. The seal on the fourth side is not designed to be easily peeled. It is primarily designed to guarantee a sterile barrier. The other three seals are made at the manufacturer and are designed to both provide a sterile barrier and be easily peel-able.

Assembled Configuration

These exemplary capsules has six different components mentioned in the previous section. The proximal and distal, are adhered together using the silicone adhesive and a loop is made at the other end of the proximal string. Once cured this string is wound up and inserted into the gelatin capsule on top of the stainless-steel ball that sits at the end of the gelatin capsule. In this example, the stainless-steel ball is in the capsule but not attached to the string, line or drag material.

To adhere the proximal and distal strings together, both strings are fanned out when the adhesive is applied so that all of the strands of the two strings are intermixed together during the adhesion process for improved interaction and durability during deployment. Simply just overlapping the strings similar to a lap solder joint does not meet the strength requirement of this interface. But when all of the strands are intermingled, the strength of the joint greatly increases allowing for full deployment and removal without separation.

In one example, during the previous development project, adhering the SS ball into the capsule would create a surface that would be exposed to the patient after dissolution of the gelatin capsule. Because of the gelatin capsule, this surface would not have been exposed to EtO gas during the sterilization process. Here the adhesive was removed from the SS ball because it was only a convenience for assembly. With the adhesive, the SS ball would not fall out of the capsule while handling the assembly.

Many different winding configurations were tested during the initial development project for this device (See for example FIG. 2). Certain configurations gave the most consistently low deployment force values. These configurations were designed so that no part of the string would interfere with the string that was in the process of deploying from the capsule. During the initial phase of the development the proximal string and interface created the most issues with deployment. The distal string would deploy with consistent and low deployment values but the combined string ends had more optimum winding configurations as indicated.

Packaging and Sterilization

Once the string has been wound up and placed into the gelatin capsule, this assembly is placed into a Tyvek/PET peel pouch. This peel pouch allows EtO gas to penetrate the Tyvek side during sterilization to prepare the device for use.

Example 2

TABLE 1

String Material

| Material | Hypoallergenic | Pros | Cons |
|---|---|---|---|
| Wool | No (Sheep fiber) | Durable | Moisture resistant Fluffy |
| Mohair | No (Goat fiber) | Durable | Expensive Fluffy |
| Cotton | Yes (If organic) | Great absorber Strong Widely manufactured | Organic is more expensive |
| Angora | No (Rabbit fiber) | Light | Expensive Small quantities produced Moisture resistant Fragile |
| Alpaca | Yes (Allergy is rare) | Durable | Moisture resistant Expensive |
| Silk | No | Durable | Delicate Expensive |
| Rayon | Yes (Allergy is rare) | Inexpensive | Absorbent Weakens when wet |
| Nylon | Yes | Durable Inexpensive Widely manufactured | Low absorbance |
| Polyester | No | Durable Inexpensive Plastic | Low absorbance |

TABLE 1-continued

| String Material | | | |
|---|---|---|---|
| Material | Hypoallergenic | Pros | Cons |
| Acrylic | Yes (Dependent on treatment) | Widely manufactured<br>Durable | Prone to pilling |
| Hemp | Yes | Durable<br>Eco-Friendly<br>Great absorber | Moderately expensive |

TABLE 2

| Capsule Materials | | | | |
|---|---|---|---|---|
| Ingredient | Vegan | Allergy | Cost | Comments |
| Gelatin | No | Possible | Low | Most common<br>Many sizes available (000-5) |

TABLE 2-continued

| Capsule Materials | | | | |
|---|---|---|---|---|
| Ingredient | Vegan | Allergy | Cost | Comments |
| Cellulose (HPMC) | Yes | Rare | Higher manufac-turing cost | Most abundant natural polymer<br>Less brittle in low humidity<br>Fast dissolution<br>Many sizes available<br>pH independent dissolution |
| Starch (potato starch) | Yes | Possible | Higher manufac-turing cost | Enteric capsules can be coated with redox materials that can deliver to the small intestine<br>Brittle when dry<br>Sizes 0-4 |
| Pullulan (tapioca) | Yes | Rare | Higher manufac-turing cost | High barrier to oxygen<br>Brittle at low humidity<br>More Sensitive than gelatin and cellulose<br>Sticky |
| Polyvinyl alcohol copolymer | Yes | Rare | Possibly lower cost | Absorbs less moisture from the air than gelatin<br>Less oxygen permeability |

TABLE 3

| Ball Weight Material | | | | | | |
|---|---|---|---|---|---|---|
| Material | Density g/cm$^3$ | MRI compatible | Corrosive | FDA Approved | Cost | Biocompatibility Ingestion info MSDS |
| Stainless Steel | | | | | | |
| Magnetic | 8.0 | No Conditional | Yes; needs chromium oxide coat | Yes; Ex. implants | Low | Non-toxic |
| Austenitic | 7.8 | | | | | |
| Titanium | 4.506 | Yes | Yes; needs oxide film coat | Yes; Ex. implants | Mode rate | Relatively non-toxic |
| Ceramic | | | | | | |
| Alumina | 3.69 | Yes | No | Yes; Ex. dental implants | Low | May cause gastrointestinal irritation |
| Zirconia | 5.68 | Yes | No | Yes; Ex. dental crowns | | May cause gastrointestinal irritation |
| Glass | 2.70 | Yes | No | Yes | Low | May cause gastrointestinal irritation |
| Cobalt-Chromium | 8.5 | Yes | No | Yes; Ex. implants | Mode rate | Chromium is toxic |
| Gold | 19.32 | Conditional | No | Yes; Ex. dental | High | Generally non-toxic |
| Silver | 10.5 | Yes | Yes | Yes; Ex. dental | High | May cause gastrointestinal irritation |
| Tantalum | 16.4 | Yes | No | Yes; Ex. implants | Mode rate | Generally considered physiologically inert |
| Platinum | 21.45 | Yes | No | Yes; Ex. implants | Very High | Low toxicity<br>May cause gastrointestinal irritation |

Example 3

In one exemplary method, the device is composed of a proximal and distal nylon string, attached to each other using adhesive that complies with FDA standard (CFR Title 21, Chapter I, Subchapter C, Parts 210-211; cGMP Drugs/ Finished Pharmaceuticals), a pharmaceutical grade gelatin capsule, and a stainless steel ball that is generally recognized to be safe for the digestive system. Morphological and functional tests were carried out on a state-of-the-art device and a device disclosed herein. Details of the various tests are also provided.

Device Design

TABLE 4

MORPHOLOGICAL AND FUNCTIONAL CHARACTERISTICS

| | Component | Property | Device |
|---|---|---|---|
| 1) | Gelatin Capsule | Size | #1 |
| | | Material | Gelatin |
| | | Type | Hard gelatin, two-piece, snap-fit |
| | | Grade | Pharmaceutical and food grade |
| | | Body Hole size (mm) | 2.0 ± 0.2 |
| | | Body Hole Location from edge (mm) | 4.2 ± 0.1 |
| | | Cap hole size (mm) | 1.9 ± 0.1 |
| 2) | Steel Ball | Size (mm) | 4.8 ± 0.1 |
| | | Material | Stainless Steel (316) |
| 3) | Proximal Yarn | Material | 100% Nylon |
| | | Construction | Single ply, multifilament |
| | | Length (cm) | 28.0 ± 0.5 |
| | | Failure Strength (N) | 48.7 ± 5.2 |
| 4) | Distal Yarn | Material | 100% Nylon |
| | | Yarn Type | 3 ply, spun |
| | | Water Absorption (% increase in weight) | 10.2 ± 0.8 |
| | | Length (cm) | 71.6 ± 0.6 |
| | | Failure Strength (N) | 52.0 ± 3.9 |
| 5) | Proximal-Distal Yarn Interface | Adhesive | Silicone based |
| | | Failure Strength (N) | 38.19 ± 3.4 |
| | | Morphology | Overlapping segments |
| 6) | Distal Yarn-Capsule Interface | Adhesive | None |
| | | Maximum Detachment Force (N) | 0.8 ± 0.5 |
| | | Adhesive | None |
| | | Attachment Mechanism | Wrapped through hole |
| 7) | Ball-Capsule Interface | Adhesive | Silicone based |
| 8) | Assembly | Sterilization | ETO |
| | | Deployment Force (N) | 0.7 ± 0.4 |

TABLE 5

Device force testing data meets or exceeds requirements for functional performance.

| Sample # | Distal Yarn Capsule Interface Maximum Detachment Force (N)-Device | Proximal-Distal Yarn Interface Strength (N)-Device | Assembly Deployment Force (N)-Device |
|---|---|---|---|
| 1 | 1.38 | 38.17 | 1.38 |
| 2 | 1.38 | 36.43 | 0.44 |
| 3 | 0.04 | 35.67 | 0.04 |
| 4 | 1.29 | 36.03 | 0.76 |
| 5 | 1.56 | 41.99 | 0.58 |
| 6 | 0.44 | 39.23 | 0.76 |
| 7 | 0.98 | 36.03 | 0.93 |
| 8 | 1.33 | 41.19 | 1.29 |
| 9 | 1.56 | 37.10 | 0.62 |
| 10 | 0.22 | 32.78 | 0.18 |

TABLE 5-continued

Device force testing data meets or exceeds requirements for functional performance.

| Sample # | Distal Yarn Capsule Interface Maximum Detachment Force (N)-Device | Proximal-Distal Yarn Interface Strength (N)-Device | Assembly Deployment Force (N)-Device |
|---|---|---|---|
| 11 | 1.33 | 44.97 | 1.33 |
| 12 | 0.04 | 41.19 | 0.22 |
| 13 | 0.53 | 32.25 | 0.53 |
| 14 | 0.67 | 42.48 | 0.62 |
| 15 | 0.58 | 40.48 | 0.53 |
| 16 | 0.53 | 39.23 | 0.36 |
| 17 | 0.31 | 39.46 | 0.80 |
| 18 | 0.04 | 39.46 | 0.27 |
| 19 | 0.62 | 33.63 | 1.11 |
| 20 | 0.89 | 36.03 | 1.07 |
| Mean | 0.79 | 38.19 | 0.69 |
| Standard Deviation | 0.53 | 3.38 | 0.39 |

Example 4: Water Absorption Data

As illustrated in the Table 6 below, the exemplary device absorbed fluid at a level that was sufficient for the key functional requirement for mucosal sampling for example, in the esophagus or other regions of the GI tract.

TABLE 6

Fluid Absorbance

| Sample # | Water Absorption (% of dry weight)-Entero Tracker |
|---|---|
| 1 | 10.63 |
| 2 | 11.15 |
| 3 | 7.78 |
| 4 | 10.81 |
| 5 | 9.32 |
| 6 | 9.94 |
| 7 | 10.94 |
| 8 | 10.36 |
| 9 | 10.49 |
| 10 | 10.57 |
| 11 | 10.87 |
| 12 | 10.73 |
| 13 | 11.01 |
| 14 | 10.14 |
| 15 | 9.73 |
| 16 | 9.44 |
| 17 | 9.94 |
| 18 | 10.62 |
| 19 | 9.84 |
| 20 | 9.14 |
| Mean | 10.17 |
| Standard Deviation | 0.82 |

Sterilizations of the devices were tested in ethylene oxide sterilization and were successful for use as pharmaceutically acceptable devices.

Devices and methods, FIGS. 2A-2J illustrate winding configurations of the line or drag material of use herein. In certain exemplary devices and methods, FIGS. 2A and 2B depict winding configurations having improved compartmentalization within a capsule, improved deployment with reduced snag.

Example 5

Performance Testing—Bench

Bench testing to optimize material, interweave design, winding configuration within the capsule, liquid absorption, pullout force, and interface detachment force, were all performed to generate the optimal device design characteristics. For the force metrics, an optimal value was developed based on analysis of the biomechanics of capsule swallowing and motion of the capsule within the gastrointestinal system due to peristaltic motion. For liquid absorption, an optimal value was developed based on evaluation of mucosal liquid rheology and capacity for the string to maximize volume capture of liquid.

Maximum Deployment Force

The Maximum Deployment Force test measures the force necessary (in Newtons) to pull the string out of the capsule without detaching the string from the capsule. An optimum value of <2.0 N was needed to ensure the string would smoothly emerge from the capsule without catching or otherwise interfering with intended performance. Lower maximum deployment forces correlate to easier capacity to pull the string out of the capsule. Clinically, this force should be as low as possible.

A force gauge is used to record the maximum force necessary to pull the string out of the capsule. The handheld gauge is hooked to the string loop which extends out of the capsule. The capsule is pulled by the operator until the entire length of string is deployed from the capsule without detaching the string from the capsule. The maximum force as displayed on the force gauge is recorded as the Maximum Deployment force. Twenty (20) post-sterilization samples were measured and the mean and standard deviation were calculated (see Table 7). Then the upper tolerance limit was calculated using normal tolerance limit calculations. Therefore, the population will perform the same or better than the predicate device for maximum deployment force with 90% Confidence and 95% Reliability.

TABLE 7

| Maximum Deployment Force | Device |
|---|---|
| Mean | 0.69N |
| Standard Deviation | 0.395 |
| 90% Conf/95% Rel Upper Tolerance Limit [MEAN + (SD * k)] | 1.564 |

Maximum Detachment Force

The Maximum Detachment Force test measures the force necessary (in Newtons) to detach the string from the capsule after it has been deployed from the capsule. This ensures the capsule does in fact release from the string within the gastrointestinal system and so is not pulled back out when the string is pulled out. Pulling the capsule back out through the throat along with the string could damage the esophagus and vocal cords. Keeping this force as low as possible ensures safe and reliable performance. Maximum detachment force of <4 N was considered optimal.

After the Maximum Deployment Force test has been conducted on a capsule, and still attached to the force gauge (tared), the capsule is again pulled until the string pulls from the capsule. The maximum force as displayed on the force gauge is recorded as the Maximum Detachment Force. Twenty (20) post-sterilization samples were measured and the mean and standard deviation were calculated (see Table 8). Then the upper tolerance limit was calculated using normal tolerance limit calculations. Therefore, the population will perform the same or better for maximum detachment force with 90% Confidence and 95% Reliability.

TABLE 8

| Maximum Detachment Force | Device |
|---|---|
| Mean | 0.79N |
| Standard Deviation | 0.531 |
| 90% Conf/95% Rel Upper Tolerance Limit [MEAN + (SD*k)] | 1.958 |

Interface Failure Strength

The Interface Failure Strength test measures the force necessary to break the seal in the string interface (the section of the string where the proximal string is adhered to the distal string). The proximal and distal string sections need to remain attached throughout the deployment and removal process to ensure safe and reliable operation of the device. A minimum interface failure strength of >23 N or greater was considered optimal.

A load frame force gauge is used to measure peak tension force in Newtons. A loop is tied in both the proximal and distal string that is big enough to fit over the jaws of the pull frame. Tension is applied to the string interface by the load frame until a failure is realized in the string interface, then the tension is stopped. The force displayed on the force gauge is recorded as the Interface Failure Strength. Twenty (20) post-sterilization samples were measured and the mean and standard deviation were calculated (see Table 9). Then the lower tolerance limit was calculated using normal tolerance limit calculations. Therefore, the population will perform the same or better than the predicate device for interface failure strength with 90% Confidence and 95% Reliability.

TABLE 9

| Interface Failure Strength | Device |
|---|---|
| Mean | 38.19N |
| Standard Deviation | 3.383 |
| 90% Conf/95% Rel Lower Tolerance Limit [MEAN − (SD * k)] | 30.721 |

Liquid Absorption Ratio

The Liquid Absorption Ratio test measures the ability of the distal string to absorb liquid and thereby achieve its intended function of sampling fluid from the gastrointestinal system. Water was used as a proxy for gastrointestinal fluid to measure this function. An absorption ration of >2 was considered optimal.

This is evaluated by comparing the weight of the water absorbed by the string and the weight of the string dry using a ratio. Twenty-four (24) inches of string is measured and cut and placed in a 20 ml vial which has been tared on a scale and weight recorded. The vial is then filled with DI water and allowed to absorb for approximately 3 hours. The water is then drained from the vial and the string is removed using tweezers and allowed to stop dripping. A new empty vial is tared and the wet string is placed within the new vial and is weighed. The ratio of the weight of the water absorbed by the string to the weight of the dry string is recorded as the Water Absorption Ratio. Twenty (20) post-sterilization samples were measured and the mean and standard deviation were calculated (see Table 12). Then the lower tolerance limit was calculated using normal tolerance limit calculations. Therefore, the population will perform the same or better than the predicate device for water absorption ratio with 90% Confidence and 95% Reliability.

TABLE 10

Water Absorption Ratio

| | Device |
|---|---|
| Mean | 10.17 |
| Standard Deviation | 0.82 |
| 90% Conf/95% Rel Lower Tolerance Limit [MEAN − (SD * k)] | 8.37 |

The device pouch in this example is a Tyvek heat seal pouch (about 4"×9") for use in EO gas sterilization (SPS Medical Supply, THP-282). The failure of the chevron seal is the most likely cause of failure of the pouch as this seal is meant to be opened by the user. SPS Medical provides a 3-year shelf life for the pouch from the date of sterilization. A preliminary heat seal strength test of 20 samples was performed in house. The data showed that the seal strength was above 1 lb of force using a lower tolerance interval analysis.

Example 6

In other exemplary devices and methods, FIGS. 3A and 3B depicts a device (100, a depicted in FIG. 1) and placement of a terminal distal end of a distal segment of the line or drag material (302) contemplated herein. FIG. 3 depicts a capsule base place over a wound line or drag (302) having the terminal distal end extending out from the capsule base (left panel, 3A) and then the terminal distal end of the distal segment is placed within a line securement opening (304) in the side wall of the base prior to a capsule cap being placed over the capsule base (right panel, 3B). FIG. 1 illustrates the terminal proximal end of the proximal segment of the line or drag protruding through the line deployment opening of the capsule cap, while the terminal distal end of the distal segment of the line or drag is depicted as releasably secured within the base through the line securement opening of the base.

Example 7

Isolation and Purification of DNA. Distal segments of a line or drag can be incubated in a lysis buffer where bacteria isolated by the device can be lysed. Total DNA can be purified and analyzed for presence or absence of an organism such as bacteria, virus, fungus or other microorganism such as pathogenic organisms.

Example 8

In some exemplary methods, presence, absence or level of proteins or antibodies can be measured using standard techniques such as ELISA, lines or drag material can be harvested by blotting to dryness, boiled in (e.g. SDS-PAGE) sample buffer, and analyzed by SDS-PAGE and/or Western blotting for the presence, level or absence of a diagnostic indicator such cytokines or other indicators of a condition or disease of the GI tract.

Example 9

In other exemplary methods, the distal segment of the line or drag material is analyzed for the presence, level or absence of diagnostic indicating cells such as mast cells or the presence of other infiltrates indicative of an infection or of cancer, for example. In some methods, trypsin/EDTA can be used to remove captured cells for further analysis and identification by methods known in the art. In certain methods, eosinophils can be detected as well as associated factors for diagnosis of a disease or condition.

Experimental Design and Methods

In certain methods, the line or drag material after deployment for a predetermined period of time can be removed and cut into pieces according to anatomical location, e.g.., mouth, esophagus, stomach, duodenum. Within the packaging for each device is a pH indicator, that when applied to the line or drag, marks the line or drag with a color change that allows for identification of the part of the GI tract that the line or drag had resided. For example, the gastric section of the string changes to orange (acidic environment) and the esophageal section is blue green (alkaline environment). The indicator is typically only applied to small (<1 mm) parts of the string and these portions will not be included in the analysis to avoid any interference with a desired assay. The length of the string from the lips to the proximal oropharynx can be measured to determine the oral section. Sections after being cut can be placed in a tube or a tray with either sample elution buffer for protein analysis or TRIZOL reagent for RNA isolation or other media or buffer for analysis. Samples can immediately be analyzed or frozen and processed in batches of 10-20 to eliminate day-to-day variability in isolation techniques, and can be stored at −80° C. for final analysis.

Protein Analyses. Proteins can be analyzed by methods known in the art and can include antibody assays to determine presence of a protein of interest.

Statistical Analyses. Samples can be compared to control samples of healthy and/or diseased subjects for assessment of a given subject and known statistical analysis techniques used for diagnosis and/or treatment of the subject.

Cytokine panels. In certain exemplary methods, cytokine panel assays can be used to detect presence, level or absence of a particular cytokine or panel of cytokines and can be measured against healthy and/or diseased subjects for analysis and treatment. In some methods, detection of IL-8 mRNA expression and/or translation can be measured alone or in combination with other cytokine markers for assessing a condition such as GERD and for example, a particular treatment regimen. It is contemplated that any treatment of GERD can be assessed using devices disclosed herein for efficacy in a subject having or at risk of developing GERD (e.g. food elimination diets or corticosteroid).

Exemplary Lateral Flow and Protein Analyses for Devices Disclosed Herein

ELISA—Most targets have commercially available ELISAs. Sources of ELISA or antibodies are noted here—CD23 (BD Bioscience), FcεRI (ELISA), Eotaxin-1,2,3(R&D Systems), Tryptase (R&D Systems).

Mesoscale—Mesoscale™ technology (Gowan et al., 2007) is a multiplex quantitative system for analyzing up to 12 target proteins in a single well of a 96-well plate. This technology needs only 2 μl of sample/well and the 96-well format allows for high throughput sampling and analysis. Data are provided in a quantitative format as pg protein per ml. For the studies, standardized Th1/Th2 templates will be used to assess the presence of Th1 (IL-2, TNF-α, IFN-γ) and Th2 (IL-4, IL-5 and IL-13) cytokines.

Immunohistochemistry—Tissue sections will undergo immunohistochemical analysis with specific antibodies as described above; antibodies for ELISA are also available for immunohistochemical analysis as previously described (Walsh et al., 1999; Desai et al., 2005; Teitelbaum et al., 2002). Briefly, all specimens will be formalin-fixed, paraffin-embedded, cut serially and either stained with hematoxylin and eosin or used for immunohistochemical studies. For immunohistochemical staining, sections will be dewaxed, rehydrated, peroxidase activity quenched, blocked and incubated with primary antibody and then secondary antibody. Color reaction will be then developed using the diaminobenzidine method and counterstained with hematoxylin, dehydrated, and mounted. Appropriate positive and negative controls will be included in each staining reaction. Quantification of positively stained cells for each of the selected antibodies will be performed.

RNA Analyses

Tissues will be homogenized with TRIZOL reagent to isolate total RNA that will then undergo reverse transcription and Q-PCR analysis using a BIORAD Real-Time iCycler PCR instrument. Primers for Th1 (IL-2, TNF-α, IFN-γ) and Th2 (IL-4, IL-5 and IL-13) cytokines have been purchased from Invitrogen.

Statistical Analyses

Linear regression will be used to model the percent change in quantity of histological eosinophilic inflammation with the change in marker level. Multiple linear regression will be used to assess the relationship of multiple markers with the pathological outcome simultaneously.

All of the methods and apparatus disclosed and claimed herein can be made and executed without undue experimentation in light of the present disclosure. While the compositions and methods of this invention have been described in terms of particular embodiments, it will be apparent to those of skill in the art that variations may be applied to the methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A device for sampling from or delivery to a gastrointestinal tract of a subject comprising:

a two-part ingestible capsule, wherein the capsule comprises a line material deployment opening;

a line material enclosed within an interior of the capsule, the line material having a proximal segment and a distal segment, wherein a distal end of the proximal segment is operably linked to a proximal end of the distal segment;

a weighted component enclosed within an interior of the capsule away from the line material deployment opening;

the line material configured for delivery through the line material deployment opening of the capsule when deployed in the gastrointestinal tract of the subject; and wherein the distal segment of the line material comprises at least a 3-ply material.

2. The device according to claim 1, wherein the proximal segment is at least one of narrower and shorter than the distal segment and remains outside an esophagus of the subject.

3. The device according to claim 1, wherein the distal segment of the line material is able to bind to at least one of proteins, polypeptides, chemicals, polynucleotides, microorganisms or by-products thereof, cells, liquid compositions, other agents or analyte located in the gastrointestinal tract.

4. The device according to claim 1, wherein at least a portion of the proximal segment extends through the line material deployment opening of the capsule, and wherein the proximal segment outside the capsule is capable of being secured in or outside of a mouth of the subject.

5. The device according to claim 1, wherein the 3-ply material comprises an absorbent fiber, mesh fiber or textured fiber.

6. The device according to claim 5, wherein the line material comprises nylon.

7. The device according to claim 1, wherein the capsule is dissolvable.

8. The device according to claim 1, wherein the two-part ingestible capsule comprises a cap and a base configured to operably mate so as to form the interior of the capsule, and wherein the line material comprises a pre-configured line for insertion into the interior of the capsule.

9. The device according to claim 8, wherein the cap further comprises a transparent feature comprising a window, and wherein a center position of the window comprises about 2.5 to about 7.5 mm distance from a rim of an open end of the base.

10. The device according to claim 1, wherein the at least the 3-ply material comprises a 3-ply nylon material.

11. The device according to claim 1, wherein each ply of the 3-ply material is the same material for sampling a GI tract of a subject.

12. The device according to claim 1, wherein the distal segment of the line material comprises a failure strength equal to or greater than 35 N when pulled at about 40 mm/minute to about 60 mm/minute to failure.

13. The device according to claim 3, wherein the distal segment of the line further comprises at least one or more capture agents and the one or more capture agents comprises an antibody, an antibody fragment, an antigen, a cytokine, a chemokine, a polynucleotide, a pharmaceutical agent, a receptor, a diagnostic or health indicator, a sensitivity or resistance indicator, a ligand or other agent, a chemical, an alloy, a metal or combination thereof.

14. The device according to claim 1, wherein the distal segment of the line when deployed in a subject associates with one or more indicators in a GI tract of the subject and the one or more indicators comprise one or more of a major basic protein (MBP), an eosinophil cationic protein (ECP), an eosinophil peroxidase (EPO), an eosinophil-derived neurotoxin (EDN), CLC/Gal-10, other eosinophil granule protein, interleukin-6 (IL-6), IL-8, IL-1β, IL-5, interferon gamma (INF-γ), other GI-associated cytokines, a chemokine, a cellular infiltrate, pH, IgE, tryptase, other marker of an allergic response, a receptor molecule, an allergen, arachidonic acid products, other inflammatory markers of the GI tract, substance P, bradykinin, other neurotransmitters of the GI tract, leukotrienes, mast cells, other GI-associated cells, bacteria, yeast, viruses, other microorganism, a metal, or combination thereof.

15. The device according to claim 1, wherein the proximal segment and distal segment comprise an adhesive compound for linking the proximal segment to the distal segment of the line material.

16. The device according to claim 1, wherein the weighted component further comprises an adhesive compound for associating the weighted component to the capsule.

17. The device according to claim 1, wherein a terminal proximal end of the proximal segment comprises a loop.

18. The device according to claim 1, wherein the device comprising the capsule, the line material and the weighted component comprises a sterilized unit.

19. A kit comprising the device according to claim 1, and at least one container.

20. A method for analyzing the gastrointestinal tract of a subject comprising, deploying the device according to claim 1 into the gastrointestinal tract of the subject; retrieving the line material and analyzing the distal segment of the line material of the device for captured diagnostic agents or health indicators from the gastrointestinal tract of the subject.

21. The method according to claim 20, wherein microbiota of the subject is analyzed.

22. The device according to claim 1, wherein the line material when enclosed within the interior of the capsule has a winding configuration comprising:

(a) a layered-loop orientation with a hole in the center, wherein loops remain separated from one another and do not overlap and the proximal end of the line is internally fed;

(b) a layered-loop orientation with a hole in the center, wherein the loops remain separated from one another and do not overlap and the proximal end of the line is externally fed;

(c) a longitudinal orientation;

(d) a random orientation;

(e) a looped configuration without layering of loops;

(f) thin, tight longitudinal layers;

(g) a twisted configuration;

(h) an interior short spool;

(i) an interior long spool; or (j) a circular configuration.

23. The device according to claim 1, wherein the line material when enclosed within the interior of the capsule has a winding configuration comprising:

(a) a layered-loop orientation with a hole in the center, wherein loops remain separated from one another and do not overlap and the proximal end of the line is internally fed;

(b) a layered-loop orientation with a hole in the center, wherein the loops remain separated from one another and do not overlap and the proximal end of the line is externally fed; or (c) a longitudinal orientation.

24. The device according to claim 1, wherein the line material enclosed within the interior of the capsule has a winding configuration comprising a layered-loop orientation with a hole in the center, wherein loops remain separated from one another and do not overlap and the proximal end of the line material is internally fed.

25. The device according to claim 1, wherein the two-part ingestible capsule comprises a cap and a base, and wherein the base further comprises a terminal securement opening, and a distal end of the line material extends from an interior of the capsule over a top surface of the base, along a perimeter of the base and through the terminal end securement opening to extend back into the interior of the base.

26. The device according to claim 1, wherein the interior of the capsule consists essentially of the line material the distal segment of the line comprising 3-ply nylon, and the weighted component.

27. The device according to claim 13, wherein the one or more capture agents, when the line or drag material is deployed in a subject, associates with one or more indicators in a GI tract of the subject and the one or more indicators comprise one or more of a major basic protein (MBP), an eosinophil cationic protein (ECP), an eosinophil peroxidase (EPO), an eosinophil-derived neurotoxin (EDN), CLC/Gal-10, other eosinophil granule protein, interleukin-6 (IL-6), IL-8, IL-1β, IL-5, interferon gamma (INF-γ), other GI-associated cytokines, a chemokine, a cellular infiltrate, pH, IgE, tryptase, other marker of an allergic response, a receptor molecule, an allergen, arachidonic arachidonic acid products, other inflammatory markers of the GI tract, substance P, bradykinin, other neurotransmitters of the GI tract, leukotrienes, mast cells, other GI-associated cells, bacteria, yeast, viruses, other microorganism, a metal, or combination thereof.

* * * * *